(12) United States Patent
Van Waeg et al.

(10) Patent No.: US 7,651,474 B2
(45) Date of Patent: Jan. 26, 2010

(54) METHOD AND APPARATUS FOR LEUKOREDUCTION OF RED BLOOD CELLS

(75) Inventors: Geert Van Waeg, Brussels (BE); Bruce W. Gibbs, Arvada, CO (US); Marc Antoon, Leuven (BE); Laura Goodrich, Lakewood, CO (US)

(73) Assignee: CaridianBCT, Inc., Lakewood, CO (US)

( * ) Notice: Subject to any disclaimer, the term of this patent is extended or adjusted under 35 U.S.C. 154(b) by 961 days.

(21) Appl. No.: 10/861,199

(22) Filed: Jun. 3, 2004

(65) Prior Publication Data
US 2004/0236263 A1 Nov. 25, 2004

Related U.S. Application Data

(63) Continuation of application No. 09/714,390, filed on Nov. 16, 2000, now abandoned, which is a continuation-in-part of application No. 09/672,519, filed on Sep. 27, 2000.

(60) Provisional application No. 60/157,360, filed on Oct. 1, 1999, provisional application No. 60/166,104, filed on Nov. 17, 1999.

(51) Int. Cl.
*A61M 37/00* (2006.01)
*C02F 1/44* (2006.01)

(52) U.S. Cl. .................. 604/6.16; 604/6.15; 604/6.01; 604/6.09; 210/645

(58) Field of Classification Search ............... 604/4.01, 604/5.01, 6.01–6.07, 6.09, 6.1, 6.11, 6.15–6.16, 604/905, 403, 406, 408, 410, 411, 264, 523, 604/533–539, 93.01; 422/44; 494/36, 37, 494/43, 45, 49, 60, 64, 76, 85, 1–7, 22
See application file for complete search history.

(56) References Cited

U.S. PATENT DOCUMENTS 4,177,149 A 12/1979 Rosenberg (Continued)

FOREIGN PATENT DOCUMENTS

DE 40 22 700 1/1992

(Continued)

OTHER PUBLICATIONS

International Search Report for PCT/US00/31501.

(Continued)

*Primary Examiner*—Leslie R Deak
(74) *Attorney, Agent, or Firm*—Laura B. Arciniegas; Edna M. O'Connor; John R. Merkling

(57) ABSTRACT

A method and apparatus for red blood collection and filtration is provided wherein a red blood cell collection assembly provides for leukoreduction filtration concurrent with or soon after the red blood cell collection procedure. The procedure preferably involves filtering the separated red blood cells in a high hematocrit (high-crit) state prior to addition of storage solution thereto. Preferably, a storage solution is passed through the leukoreduction filter after the RBCs have been filtered therethrough. The red blood cell collection filtration and storage assembly is preferably preconnected to a blood component separation disposable assembly, including, for example, a centrifuge vessel and a blood removal/return assembly for removing blood from a donor, passing the blood to the centrifuge vessel for separation of the blood into components for collection and providing for filtration of the separated red blood cell component, as described.

1 Claim, 14 Drawing Sheets

U.S. PATENT DOCUMENTS

| | | | |
|---|---|---|---|
| 4,197,847 A | | 4/1980 | Djerassi |
| 4,267,269 A | * | 5/1981 | Grode et al. .................. 435/2 |
| 4,360,435 A | | 11/1982 | Bellamy et al. |
| 4,400,277 A | | 8/1983 | Leason |
| 4,596,657 A | | 6/1986 | Wisdom |
| 4,680,025 A | | 7/1987 | Kruger et al. |
| 4,701,267 A | | 10/1987 | Watanabe et al. |
| 4,767,541 A | | 8/1988 | Wisdom |
| 4,810,378 A | | 3/1989 | Carmen et al. |
| 4,855,063 A | | 8/1989 | Carmen et al. |
| 4,880,548 A | | 11/1989 | Pall et al. |
| 4,915,848 A | | 4/1990 | Carmen et al. |
| 4,919,823 A | | 4/1990 | Wisdom |
| 4,923,620 A | | 5/1990 | Pall |
| 4,925,572 A | | 5/1990 | Pall |
| 4,936,998 A | | 6/1990 | Nishimura et al. |
| 4,943,287 A | | 7/1990 | Carmen |
| 4,985,153 A | | 1/1991 | Kuroda et al. |
| 4,997,577 A | | 3/1991 | Stewart |
| 5,009,654 A | * | 4/1991 | Minshall et al. .............. 604/410 |
| 5,034,135 A | * | 7/1991 | Fischel ....................... 210/651 |
| 5,089,146 A | | 2/1992 | Carmen et al. |
| 5,092,996 A | | 3/1992 | Spielberg |
| 5,100,551 A | | 3/1992 | Pall et al. |
| 5,100,564 A | | 3/1992 | Pall et al. |
| 5,104,788 A | | 4/1992 | Carmen et al. |
| 5,126,054 A | | 6/1992 | Matkovich |
| 5,152,905 A | | 10/1992 | Pall et al. |
| 5,180,504 A | | 1/1993 | Johnson et al. |
| 5,217,627 A | | 6/1993 | Pall et al. |
| 5,229,012 A | | 7/1993 | Pall et al. |
| 5,236,716 A | | 8/1993 | Carmen et al. |
| 5,252,222 A | | 10/1993 | Matkovich et al. |
| 5,258,126 A | | 11/1993 | Pall et al. |
| 5,258,127 A | | 11/1993 | Gsell et al. |
| 5,269,946 A | | 12/1993 | Goldhaber et al. |
| 5,281,342 A | | 1/1994 | Biesel et al. |
| 5,300,060 A | | 4/1994 | Nelson |
| 5,302,299 A | | 4/1994 | Pascale et al. |
| 5,316,674 A | | 5/1994 | Pall et al. |
| 5,344,561 A | | 9/1994 | Pall et al. |
| 5,360,545 A | | 11/1994 | Pall et al. |
| 5,362,406 A | | 11/1994 | Gsell et al. |
| 5,364,526 A | | 11/1994 | Matkovich et al. |
| 5,399,268 A | | 3/1995 | Pall et al. |
| 5,403,272 A | | 4/1995 | Deniega et al. |
| 5,431,814 A | | 7/1995 | Jorgensen |
| 5,445,736 A | | 8/1995 | Pall et al. |
| 5,451,321 A | | 9/1995 | Matkovich |
| 5,470,488 A | | 11/1995 | Matkovich et al. |
| 5,472,621 A | | 12/1995 | Matkovich et al. |
| 5,501,795 A | | 3/1996 | Pall et al. |
| 5,512,187 A | | 4/1996 | Buchholz et al. |
| 5,527,472 A | | 6/1996 | Bellotti et al. |
| 5,536,238 A | | 7/1996 | Bischof |
| 5,543,062 A | | 8/1996 | Nishimura |
| 5,545,339 A | | 8/1996 | Bormann et al. |
| 5,547,591 A | | 8/1996 | Hagihara et al. |
| 5,549,834 A | | 8/1996 | Brown |
| 5,580,465 A | | 12/1996 | Pall et al. |
| 5,587,070 A | | 12/1996 | Pall et al. |
| 5,601,730 A | | 2/1997 | Page et al. |
| 5,616,254 A | | 4/1997 | Pall et al. |
| 5,630,946 A | | 5/1997 | Hart et al. |
| 5,670,060 A | | 9/1997 | Matkovich et al. |
| 5,674,173 A | | 10/1997 | Hlavinka et al. |
| 5,690,815 A | | 11/1997 | Krasnoff et al. |
| 5,695,653 A | | 12/1997 | Gsell et al. |
| 5,722,926 A | | 3/1998 | Hlavinka et al. |
| 5,738,796 A | | 4/1998 | Bormann et al. |
| 5,744,047 A | | 4/1998 | Gsell et al. |
| 5,762,791 A | * | 6/1998 | Deniega et al. ........ 210/321.67 |
| 5,769,839 A | | 6/1998 | Carmen et al. |
| 5,783,085 A | * | 7/1998 | Fischel ....................... 210/651 |
| 5,836,934 A | | 11/1998 | Beshel |
| 5,863,436 A | | 1/1999 | Matkovich |
| 5,865,785 A | | 2/1999 | Bischof |
| 5,876,605 A | * | 3/1999 | Kitajima et al. ............. 210/650 |
| 5,902,490 A | | 5/1999 | Zuk, Jr. |
| 5,906,570 A | | 5/1999 | Langley et al. |
| 5,913,768 A | | 6/1999 | Langley et al. |
| 5,939,319 A | | 8/1999 | Hlavinka et al. |
| 5,948,278 A | | 9/1999 | Sammons et al. |
| 5,951,877 A | | 9/1999 | Langley et al. |
| 5,954,971 A | * | 9/1999 | Pages et al. .................. 210/739 |
| 6,030,539 A | | 2/2000 | Zuk, Jr. |
| 6,051,147 A | | 4/2000 | Bischof |
| 6,053,856 A | | 4/2000 | Hlavinka |
| 6,053,885 A | | 4/2000 | Beshel |
| 6,071,421 A | | 6/2000 | Brown |
| 6,071,422 A | | 6/2000 | Hlavinka et al. |
| 6,080,322 A | | 6/2000 | Deniega et al. |
| 6,200,287 B1 | * | 3/2001 | Keller et al. ............... 604/6.01 |
| 6,251,284 B1 | * | 6/2001 | Bischof et al. .............. 210/739 |
| 6,322,488 B1 | * | 11/2001 | Westberg et al. ............. 494/43 |
| 6,334,842 B1 | | 1/2002 | Hlavinka et al. |
| 6,354,986 B1 | | 3/2002 | Hlavinka et al. |
| 6,361,692 B1 | | 3/2002 | Bischof |
| 2002/0090319 A1 | | 7/2002 | Vandlik et al. |
| 2003/0205517 A1 | | 11/2003 | Bischof |

FOREIGN PATENT DOCUMENTS

| | | |
|---|---|---|
| DE | 40 22 700 A1 | 1/1992 |
| DE | 43 08 880 | 9/1993 |
| DE | 43 08 880 A1 | 9/1993 |
| EP | 0 243 744 | 11/1987 |
| EP | 0 243 744 A2 | 11/1987 |
| EP | 0 266 683 | 5/1988 |
| EP | 0 331 174 | 9/1989 |
| EP | 0 331 174 A1 | 9/1989 |
| EP | 0 397 403 | 11/1990 |
| EP | 0 406 485 | 1/1991 |
| EP | 0 408 462 | 1/1991 |
| EP | 0 419 346 | 3/1991 |
| EP | 0 442 114 | 8/1991 |
| EP | 0 508 474 | 10/1992 |
| EP | 0 852 151 | 7/1998 |
| EP | 0 958 838 | 11/1999 |
| EP | 1 230 940 | 11/2000 |
| EP | 0 578 086 | 1/2001 |
| FR | 2 695 037 | 9/1993 |
| FR | 2 695 037 A1 | 9/1993 |
| WO | WO 91/04088 | 4/1991 |
| WO | WO 91/17809 | 11/1991 |
| WO | WO 92/07656 | 5/1992 |
| WO | WO 93/08904 | 5/1993 |
| WO | WO 93/24157 | 12/1993 |
| WO | WO 93/25295 | 12/1993 |
| WO | WO 94/25086 | 11/1994 |
| WO | WO 94/28996 | 12/1994 |
| WO | WO 95/23016 | 8/1995 |
| WO | WO 96/20020 | 7/1996 |
| WO | WO 96/33023 | 10/1996 |
| WO | WO 98/28057 | 7/1998 |
| WO | WO 98/41087 | 9/1998 |
| WO | WO 98/50163 | 11/1998 |
| WO | WO 99/11305 | 3/1999 |
| WO | WO 99/26678 | 6/1999 |
| WO | WO 99/53975 | 10/1999 |
| WO | WO 00/54824 | 9/2000 |
| WO | WO 00/54886 | 9/2000 |
| WO | WO 01/24848 | 4/2001 |
| WO | WO 01/36022 | 5/2001 |

| | | |
|---|---|---|
| WO | WO 02/43790 | 6/2002 |

OTHER PUBLICATIONS

"LRF6/LRF10, High Efficiency Leukocyte Removal Filter Systems for Platelets", PALL Biomedical Products Corporation.

"Press Release: Advanced Blood Collection Device Now Offers Pre-Attached Filtration", Feb. 2000.

Antoon et al, "High-crit Filtration of Trima Red Blood Cells: Preliminary Results of a Multicenter Trial".

Aubuchon et al, "Cost-Effectiveness of Leukocyte Depletion of Blood Components", Presented at the 1993 AABB Meeting Miami Beach, FL.

Barz et al, "Leucocyte Depletion of Red Cell Concentrates Evaluation of Conventional Filters and a Closed In-line System", pp. 205-209.

Beltzig et al, "Preparation of Leucocyte Depleted Red Blood Cell Concentrates Using Optipac Bloodbags with Integral Filter", pp. 201-203.

Besso et al., "Asahi Sepacell R-500 Leukocyte Removal Filter: The Effects of Saline Flush on the Unloading of White Blood Cells and Contamination of the Filtrate".

Bock et al, "The CMV Problem: The Role of Leucocyte Depletion in Minimising the Risk of CMV Transmission in Transfusion Medicine", pp. 97-101.

Brozovic, B., "Cost Effectiveness of Leucocyte Depletion", p. 125-129.

Bruil et al., "Asymmetric Membrane Filters for the Removal of Leukocytes From Blood", *J. Biomed. Materials Research*, vol. 25, 1459-1480, 1991.

Dittman et al, "Automated Blood Component Collection—Concurrent Collection of Red Cell Concentrates Leucoreduced Single Donor Platelets and Plasma Using the New COBE Trima System", $32^{nd}$ Annual Meeting, Deutsche Gesellshaft fur Transfusionsmedizin und Immunhamatologie (DGTI), Oct. 5-8, 1999, p. 4.30.

Dzik, Leukodepletion Blood Filters: Filter Design and Mechanisms of Leukocyte Removal, *Transfusion Medicine Reviews*, vol. VII, No. 2, Apr. 1993, pp. 65-77.

Ferry et al, "Quality Support for RBC Leukoreduction by a Filter Manufacturer", ISBT Meeting, 1 page.

Freedman et al., White Cell Depletion of Red Cell and Pooled Random-Donor Platelet Concentrates by Filtration and Residual Lymphocyte Subset Analysis, *Transfusion*, 1991, vol. 31, No. 5, pp. 433-440.

Getter et al, "Evaluation of the COBE Trima Automated Blood Component", AABB 2000 Abstract No. 538.

Gibbs, Bruce, "Leukoreduction of Trima Collection System Packed Red Blood Cell Products with Hemasure R\LS after Overnight Refrigeration", Abstract No. 539.

Glaser et al, "Effectiveness of White Cell Reduction by Filtration with Respect to Blood Storage Time and Blood Product Temperature", p. 155-159.

Haemonetics, "Only Haemonetics delivers residual White Blood Cell counts for platelet apheresis consistently below $5 \times 10^5$ and always below $5 \times 10^6$" Sep. 1992.

Hogman, Claes, "Leucocyte Depletion of Blood Components", p. 1-4.

Marshall et al, "Microaggregate Formation in Stored Blood. III: Comparison of Bentley, Fenwall, Pall and Swank Micropore Filtration", *Circulatory Shock*, vol. 2, No. 4, 1975, pp. 249-263.

Matthes, G., "The Future of Leucocyte Depletion: In-line Filtration", pp. 115-123.

McAteer et al, "Variability in Hematocrit Measurements on Packed RBC Units: Effects of Method, EDTA, Dilution, and Storage Solution," Abstract 540.

Normandin et al, Controlled Introduction of a new RBC Leukoreduction Filter, ISBT Meeting, 1 page.

Nossaman et al, "Measured Success with New Filter Implementation", AABB 2000 Meeting, Abstract No. 100607.

Nossaman, Janis, "Implementation of the COBE R\LS Pre-storage Leukoreduction Filter: Evaluation of Product Performance During Process Validation", AABB 2000 Meeting, Abstract No. 100618.

Riggert et al, High-crit In-process Filtration of Red Blood Cell Concentrates Produced by an Automated Blood Collection System, ISBT 2000, p. 293.

Sakalas, et al., Evaluation of Two New High Performance Leucocyte Removal Filters (ASAHI PLS-5A PLS-10A) for Use with Platelet Components, pp. 161-165.

Seghatchian et al., Leucocyte Depletion by Filtration is Associated with Changes in Platelet Aggregation States: A New Diagnostic Approach, pp. 171-173.

Seghatchian, et al., Leucocyte Depletion of Platelet Concentrates: Is Poor Filtration Recovery Related to Activation/Aggregation States of Platelets?, pp. 167-170.

Sekiguchi, S, "Aspects of Leucocyte Depletion of Blood Components: Present Status in Japan" pp. 19-27.

Sirchia, G, "Clinical Experience of White Cell Reduction in Blood Components: An Overview", p. 59-75.

Sniecinski, Prevention of Immunologic and Infectious Complications of Transfusion by Leukocyte Depletion, Prevention of Complications of Transfusion, Chapter 18; pp. 202-211.

Van Waeg et al, On-line High-crit Filtration of Red Cells Collected on the COBE Trima, Abstract No. 500014.

Van Wie, et al., The Effect of Hematocrit and Recycle on Cell Separations, Plasma, *Ther. Transfus. Technol*. 1986; 7:373-388.

Wenz, Barry, "Leukocyte-Free Red Cells: The Evolution of a Safer Blood Product", *Controversies of Leukocyte-Poor Blood and Components*, editor, McCarthy et al, Am Assoc of Blood banks, 1989, pp. 27-49.

\* cited by examiner

METHOD AND APPARATUS FOR LEUKOREDUCTION OF RED BLOOD CELLS

PRIORITY CLAIM

This application is a continuation of U.S. application Ser. No. 09/714,390, filed Nov. 16, 2000 (now abandoned) which is a continuation-in-part of U.S. application Ser. No. 09/672,519, filed Sep. 27, 2000 which claims the benefit of U.S. Provisional Application No. 60/157,360, filed Oct. 1, 1999 and U.S. Provisional Application No. 60/166,104, filed Nov. 17, 1999.

FIELD OF INVENTION

The present invention relates generally to the field of extracorporeal blood processing methods and apparatus which are particularly useful in blood component collection, and more particularly, the present invention relates to methods and apparatus for the leukoreduction of red blood cells preferably collected with an apheresis system.

BACKGROUND OF THE INVENTION

One well-known type of extracorporeal blood processing involves an apheresis system and/or procedure in which blood is removed from a donor or a patient (hereafter cumulatively referred to as a donor), directed to a blood component separation device (e.g., centrifuge), and separated into various blood component types (e.g., red blood cells, white blood cells, platelets, plasma) for collection or therapeutic purposes. One or more or all of these blood component types may either be collected, and/or treated for therapeutic purposes before storage or return to a patient, while the remainder may simply be returned to the donor or patient.

A number of factors may affect the commercial viability of an apheresis system. One factor relates to the time and/or expertise required of an individual to prepare and operate the apheresis system. For instance, reducing the time required by the operator to complete an entire collection procedure, as well as reducing the complexity of these actions, can increase productivity and/or lower the potential for operator error. Moreover, reducing the dependency of the system on the operator may further lead to reductions in the credentials desired/required for the operators of these systems.

Donor-related factors may also impact the commercial viability of an apheresis system and include, for example, donor convenience and donor comfort. For instance, donors/patients may have a limited amount of time which may be committed to a donation or therapeutic procedure. Consequently, once at the collection or treatment facility, the amount of time which is actually spent collecting and/or treating blood components is an important consideration. This also relates to donor comfort as the actual collection procedure may be somewhat discomforting because at least one and sometimes two access needles are disposed in the donor throughout the procedure.

Performance-related factors also affect the commercial viability of an apheresis system. Performance may be judged in terms of the collection efficiency of the apheresis system, which may impact or improve product quality and/or may in turn reduce the amount of processing time and thus decrease operator burden and increase donor convenience. The collection efficiency of a system may of course be gauged in a variety of ways, such as by the amount of a particular blood component type which is collected in relation to the quantity of this blood component type which passes through the apheresis system. Performance may also be evaluated based upon the effect which the apheresis procedure has on the various blood component types. For instance, it is desirable to minimize the adverse effects on the blood component types as a result of the apheresis procedure (e.g., reduce platelet activation).

Another performance-related factor is the end quality of the collected blood component. For example, if red blood cells are the component to be collected, it is generally desirable that such red blood cells be leukoreduced by the removal of white blood cells or leukocytes. White blood cells can present problems to the ultimate recipient of the collected blood component. Transfused products containing white blood cells can provoke immunogenic reactions and viral diseases. Conventionally, filters have been used to remove leukocytes from collected blood products or components. For example, U.S. Pat. No. 5,954,971 discloses the use of a filter with an apheresis system for filtering a diluted blood component prior to collection. Other distinctive methods have also been used, and these have generally dictated special preliminary steps such as pre-chilling and/or overnight storage of collected components prior to filtration. Another distinct conventional filtration step is the venting or air handling/re-circulation or by-passing at the end of the filtration procedure which had been deemed important for substantial recovery of a remainder portion of the blood component to be processed through a red blood cell filter. An apparatus and method for red blood cell filtration in conjunction with apheresis separation is also disclosed in the commonly-owned U.S. patent application Ser. No. 09/672,519, filed Sep. 27, 2000; the disclosure hereof is incorporated by reference herein as if fully set forth. Further background on apheresis red blood cell separation and collection can be found in the PCT publication WO99/11305, which is also incorporated herein by this reference.

SUMMARY OF THE INVENTION

The present invention generally relates to extracorporeal blood processing. Since each of the various aspects of the present invention may preferably be incorporated into an apheresis system (e.g., whether for blood component collection in which "healthy" cells or other blood components are removed from the donor blood for later transfusion, or for therapeutic "unhealthy" blood component removal), the present invention will be described in preferred relation to such apheresis systems. Apheresis may often imply the return of certain blood components back to the donor. However certain aspects of the present invention may be suited for extracorporeal blood processing applications in which all donated blood components are retained and such are also intended within the scope of the present invention.

An apheresis system which may be used with and/or in one or more aspects of the present invention generally includes at least a blood component separation device (e.g., a membrane-based separation device, and/or a rotatable centrifuge element, such as a rotor and channel combination), which provides the mechanism and/or the forces required to separate blood into its various blood component types (e.g., red blood cells, white blood cells, platelets, and/or plasma). In one preferred embodiment, the separation device includes a centrifuge channel which receives a disposable blood processing vessel. Typically, a donor or perhaps a patient (collectively referred to hereafter as a donor) is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor and directed to the blood component separation device such that at least one type of blood component may be separated and removed from the blood, either for collection or for therapy.

One aspect of the present invention relates to an extracorporeal blood processing device which is used to provide leukoreduced red blood cells, that in one embodiment comprises a disposable assembly which may include one or more flexible tubing lines adjacently interconnected to a blood processing vessel, a collection container interconnected to one of the flexible tubing lines, and a filtration device for filtering a selected separated blood component type such as separated high hematocrit red blood cells. In one embodiment, multiple sets of corresponding first and second tubing lines and collection and/or intermediate containers are provided, with each of the sets providing for selective collection of a blood component in a separate collection container or for diversion back to the donor. Use of such an arrangement yields a compact disposable assembly that can be readily mounted relative to the blood component separation machine in a reliable manner. The tubing lines may also be interconnected to a disposable cassette member.

Another aspect of the present invention relates to the extracorporeal separation and collection of red blood cells using an apheresis blood processing system. More particularly, a method for such separation and collection includes separating high hematocrit red blood cells from the blood within a blood processing vessel of a blood component separation machine and collecting at least a portion of the separated red blood cells within a red blood cell collection container that is disparate from yet preconnected via tubing lines to the blood processing vessel. Such red blood cells may be separated and collected alone, or prior or subsequent to or concurrently with other blood components such as platelets and/or plasma. According to the present invention, before the ultimate collection of the red blood cells in the collection container, the red blood cells are filtered through a filtration device. This filtration preferably occurs during the overall separation procedure, although it could be initiated soon thereafter. Nevertheless, the separation procedure may be a continuous or batch process, and in either case, the filtration occurs upon or soon after removal of the separated high hematocrit red blood cells from the processing vessel, yet preferably concurrently with or soon after the overall separation process. In a continuous separation process, this high hematocrit red blood cell filtration can be continually-performed during the continual separation and removal of the separated red blood cells from the processing vessel. In this context, the word "after" means only post-separation in the separation vessel; it does not mean that the entire separation process must be completed prior to filtration.

A further aspect of the invention relates to an apheresis disposable assembly including a leukoreduction filter for filtering the high hematocrit red blood cell component to be collected. In conjunction with this aspect, the instant invention provides a preconnected disposable assembly comprising a separation vessel for separating blood into components, a fluid flow cassette with internal passageways and a leukoreduction filter for filtering high hematocrit separated red blood cells upon or soon after removal of those red blood cells from the separation vessel yet preferably concurrently with or soon after the overall separation process. As above, the adverbial modifier "after" is intended to mean only post-separation, not requiring the entire overall separation process to be complete.

Still one further aspect of the present invention relates to a method for using a preconnected disposable assembly which includes a leukoreduction filter. This method generally involves passing separated and/or intermediately collected high hematocrit red blood cells through the filter within a short time period after separation of the red blood cells from donor blood. Another aspect of this method includes the option of rinsing or flushing an additive or storage solution through the leukoreduction filter after completion of the red blood cell filtration through the leukoreduction filter.

In another aspect, the separated red blood cells are filtered in a high hematocrit state as they exist after separation in the apheresis system. Here also, filtration may take place during or soon after the overall apheresis process. As above, the phrase "after separation" here does not require completion of the entire separation process. An additive/storage solution may be and preferably is added to the red blood cells after such filtration. The additive/storage solution is also preferably flushed through the filter after the red blood cells are filtered therethrough.

These and still further aspects of the present invention are more particularly described in the following description of the preferred embodiments presented in conjunction with the attached drawings which are described briefly below.

DETAILED DESCRIPTION

The present invention will be described in relation to the accompanying drawings which assist in illustrating the pertinent features hereof. Generally, the primary aspects of the present invention relate to both procedural and structural improvements in or a sub-assembly for use with a blood apheresis system. However, certain of these improvements may be applicable to other extracorporeal blood processing applications whether any blood components are returned directly to the donor or otherwise; and such are within the scope of the present invention as well.

Figure 1:
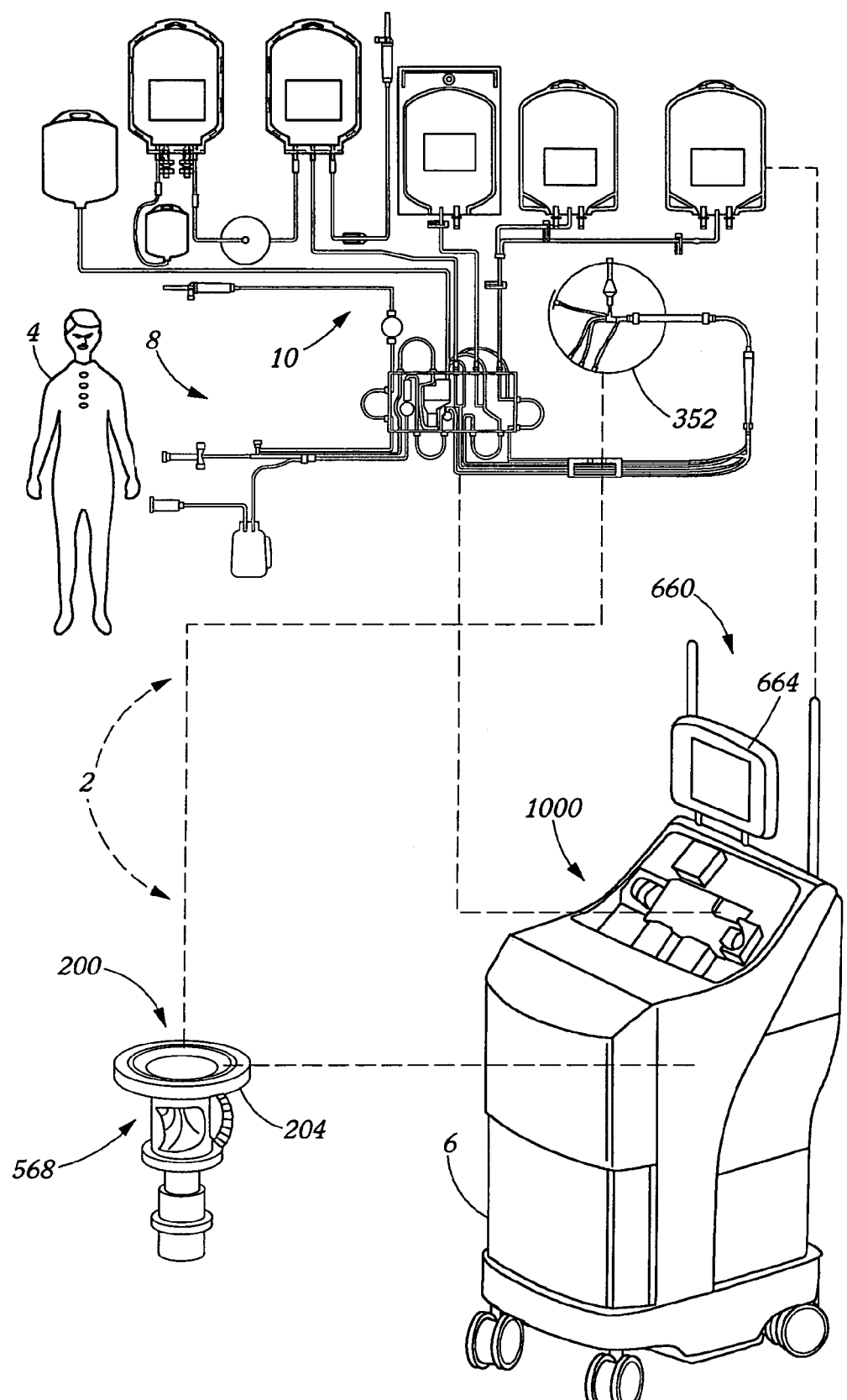
FIG. 1 is a schematic view of one embodiment of an apheresis system which can be used in or with the present invention.

A preferred blood apheresis system 2 for use in and/or with the present invention is schematically illustrated in FIG. 1. System 2 preferably provides for a continuous blood component separation process. Generally, whole blood is withdrawn from a donor 4 and is substantially continuously provided to a blood component separation device 6 where the blood is continuously separated into various component types and at least one of these blood component types is preferably continuously collected from the device 6. These blood components may then be provided for collection and subsequent use by another through transfusion or may either be uncollected and then be returned to the donor 4. Therapeutic treatment and return of certain blood components is a viable, yet less preferred alternative use hereof as well.

In the blood apheresis system 2, blood is withdrawn from the donor 4 and directed through a preconnected disposable set 8 which includes an extracorporeal tubing circuit 10 and, in the preferred embodiment, a blood processing vessel 352 which together define a completely closed, sterile and disposable system. The disposable set 8 is mounted on and/or in the blood component separation device 6 which preferably includes a pump/valve/sensor assembly 1000 for interfacing with the extracorporeal tubing circuit 10, and a channel assembly 200 for interfacing with the disposable blood processing vessel 352.

The channel assembly 200 may include a channel housing 204 which is rotatably interconnected with a rotatable centrifuge rotor assembly 568 which provides the centrifugal forces required to separate blood into its various blood component types by centrifugation. The blood processing vessel 352 may then be interfitted within the channel housing 204. When thus connected as described, blood can then be flowed substantially continuously from the donor 4, through the extracorporeal tubing circuit 10, and into the rotating blood processing vessel 352. The blood within the blood processing vessel 352 may then be continuously separated into various blood component types and at least one of these blood component types (e.g., platelets, plasma, or red blood cells) is preferably continually removed from the blood processing vessel 352. Blood components which are not being retained for collection or for therapeutic treatment (e.g., platelets and/or plasma) are preferably also removed from the blood processing vessel 352 and returned to the donor 4 via the extracorporeal tubing circuit 10. Note, various alternative apheresis systems (not shown) may also make use of the present invention; including batch processing systems (non-continuous inflow of whole blood or outflow of separated blood components) or smaller scale RBC/plasma separation systems, even if no blood components may be returned to the donor.

Operation of the blood component separation device 6 is preferably controlled by one or more processors included therein, and may advantageously comprise a plurality of embedded computer processors to accommodate interface with ever-increasing PC user facilities (e.g., CD ROM, modem, audio, networking and other capabilities). Relatedly, in order to assist the operator of the apheresis system 2 with various aspects of its operation, the blood component separation device 6 preferably includes a graphical interface 660 preferably with an interactive touch screen 664.

Further details concerning the operation of a preferred apheresis system, such as the COBE Trima® System (available from the assignee of this application, Gambro, Inc., Lakewood, Colo.) may be found in a plurality of publications, including, for example, WO99/11305 and U.S. Pat. No. 5,653,887; No. 5,676,644; No. 5,702,357; No. 5,720,716; No. 5,722,946; No. 5,738,644; No. 5,750,025; No. 5,795,317; No. 5,837,150; No. 5,919,154; No. 5,921,950; No. 5,941,842; and No. 6,129,656; among numerous others. The disclosures hereof are incorporated herein as if fully set forth. A plurality of other known apheresis systems may also be useful herewith, as for example, the Baxter CS3000® and/or Amicus® and/or Autopheresis-C® systems, and/or the Haemonetics MCS® or MCS®+ and/or the Fresenius COM.TEC™ or AS-104™ and/or like systems.

Disposable Set: Extracorporeal Tubing Circuit

Figure 2A:
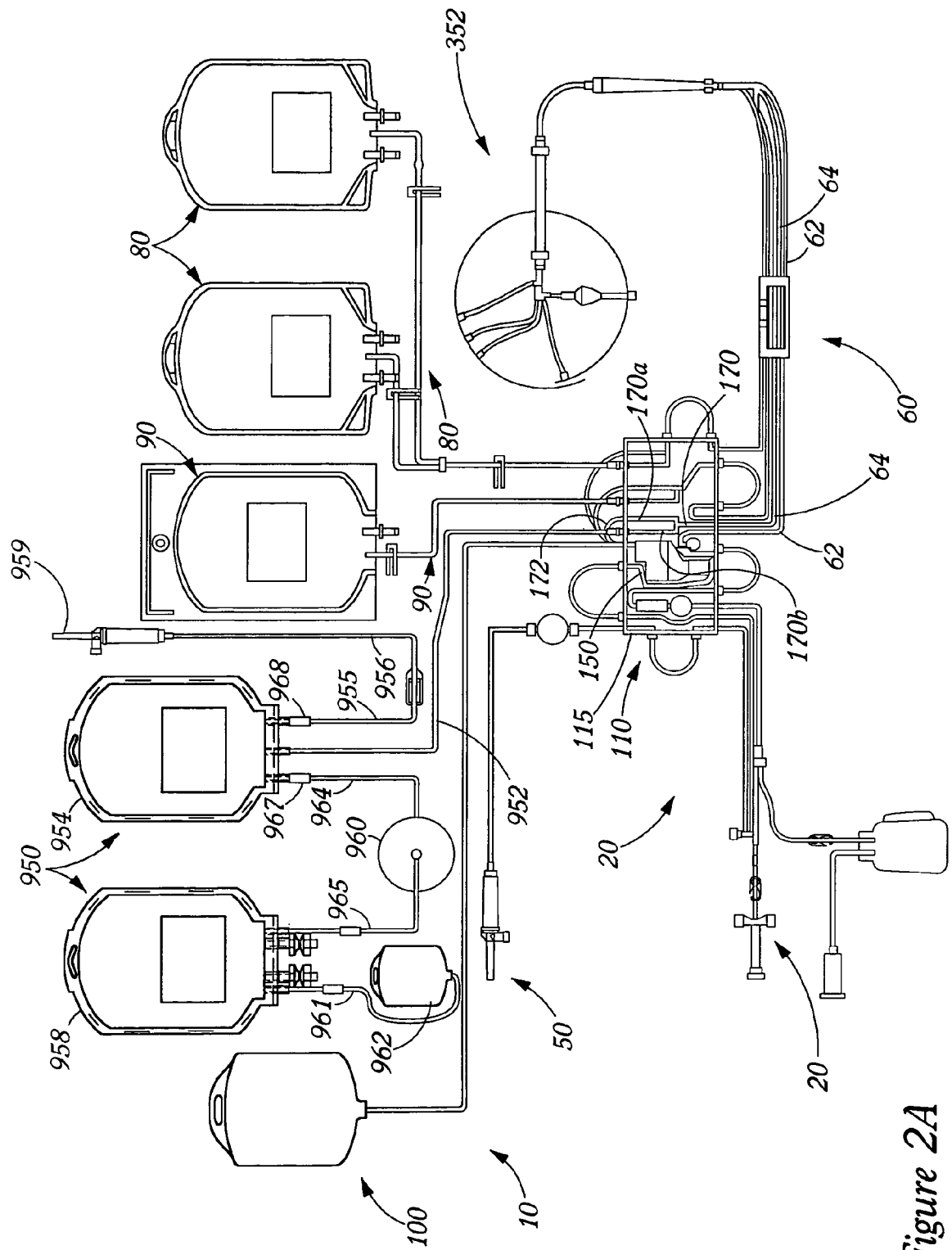
FIGS. 2A-2B illustrate an extracorporeal tubing circuit, cassette assembly, and filter and collection bag assembly thereof for use with the system of FIG. 1 pursuant to the present invention.
Figure 2B:
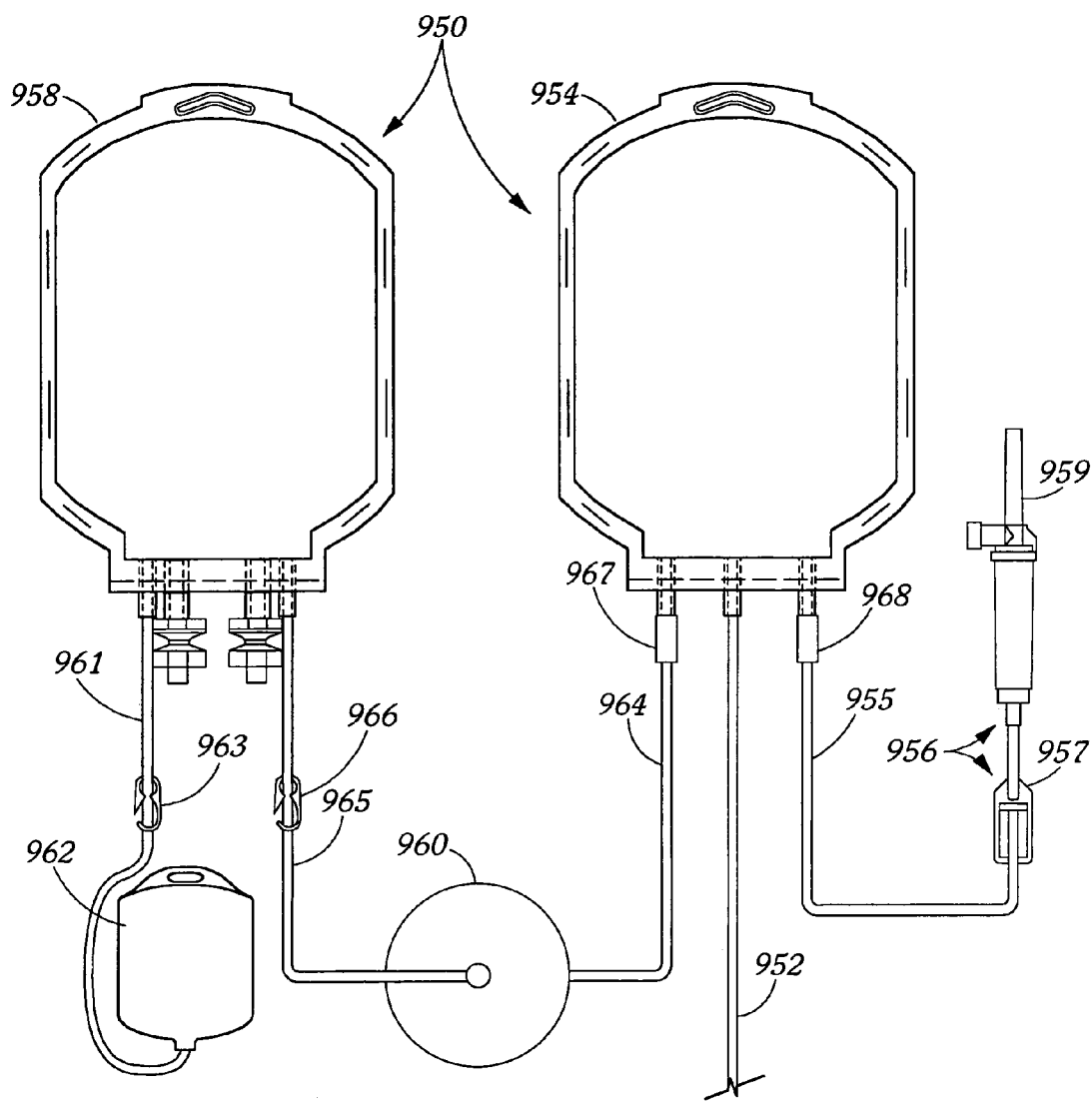

As illustrated in FIGS. 2A-2B, a preferred preconnected extracorporeal tubing circuit 10 may include a cassette assembly 110 and a number of tubing/collection assemblies 20, 50, 60, 80, 90, 950 and 100 interconnected therewith. Preferably, a blood removal/return tubing assembly 20 provides a single needle interface between a donor 4 and the remainder of the tubing circuit 10 (although a two-needle set-up may also be used). The preferred embodiment includes a cassette assembly 110, which is interconnected between the tubing assembly 20 which connects the donor 4 thereto, and blood inlet/blood component tubing line sub-assembly 60 which provides the interface between cassette assembly 110 and blood processing vessel 352. An anticoagulant tubing assembly 50, a platelet collection tubing assembly 80, a plasma collection tubing assembly 90, a red blood cell collection assembly 950 and a vent bag tubing line sub-assembly 100 are also preferably interconnected with cassette assembly 110 in this embodiment. As will be appreciated, the extracorporeal tubing circuit 10 and blood processing vessel 352 are preferably pre-interconnected to combinatively yield a closed, pre-sterilized disposable assembly for a single use.

The disclosures of the above-listed patents include numerous further details of the preferred apheresis system for use with the present invention. Such details are not repeated here except for certain of those which may relate particularly to red blood cell (hereafter, RBC) collection and/or other RBC processes.

For example, emanating from vessel 352 is an RBC outlet tubing line 64 of the blood inlet/blood component tubing assembly 60 which is interconnected with integral RBC passageway 170 of cassette 115 of cassette assembly 110 (see FIG. 2A). The integral RBC passageway 170 includes first and second spurs 170a and 170b, respectively. The first spur 170a is interconnected with RBC return tubing loop 172 to return separated RBCs to a donor 4. For such purpose, the RBC return tubing loop 172 is preferably interconnected to the top of a blood return reservoir 150 of the cassette assembly 110. The second spur 170b may, as preferred herein, be connected with an RBC collection tubing assembly 950 (see FIGS. 2A and 2B) for collecting RBCs during use. RBC collection tubing assembly 950 preferably includes RBC collector tubing line 952 which communicates with spur 170b, an intermediate RBC collection reservoir or bag 954, an RBC filtration sub-assembly including an ultimate RBC collection reservoir or bag 958, an RBC leukoreduction filter 960 and an air removal bag 962. A sterile barrier filter/drip spike assembly 956 preferably including a sterile barrier 957 and a spike 959, may also be included for connecting to a source of additive solution, inter alia, and may be connected to RBC bag 954 through tubing line 955 and an optional frangible connector 968 as will be described in more detail below. Bags 954 and 958 are connected to each other by two tubing lines 964, 965 between and to each of which the RBC leukoreduction filter 960 is connected. A clamp 966 may be included on line 965. Collection bag 954 may be, in one less preferred embodiment, interconnected to RBC filter 960 through a frangible connector 967. The air removal bag 962 is attached to the RBC collection bag 958 by a tubing line 961 which may have a clamp 963 attached thereto. The RBC collection tubing line, filter and container sub-assembly 950 is preferably a preconnected part of the disposable assembly 8/10.

Figure 2C:
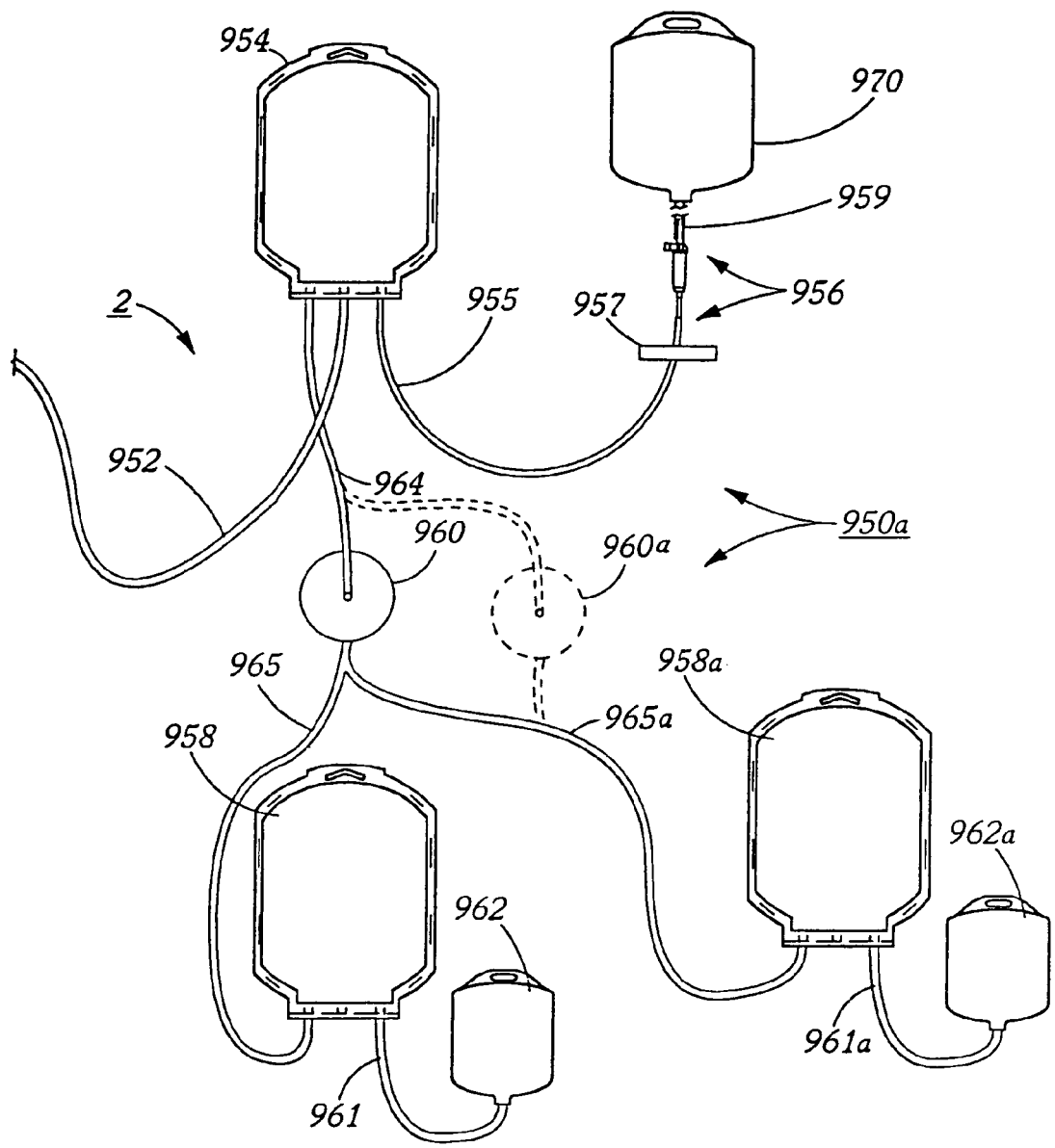
FIG. 2C illustrates an alternative extracorporeal tubing circuit filter and collection bag assembly for use according to the present invention.

An alternative tubing set filter and collection bag assembly 950a is shown in FIG. 2C and includes a second collection bag 958a connected via a Y-type of connection to filter 960, via the branch tubing line 965a. A further air bag 962a is preferably connected to the second bag 958a via a tubing line 961a. More details particularly as to the use hereof will be set forth below.

Most portions of the tubing assemblies 20, 50, 60, 80, 90, 100 and 950 and cassette assembly 110 are preferably made from plastic components including, for example, polyvinyl chloride (PVC) tubing lines, that permit visual observation and monitoring of blood/blood components therewithin during use. It should be noted that thin-walled PVC tubing may be employed for approved, sterile docking (i.e., the direct connection of two pieces of tubing line) for the RBC collector tubing lines 952, 964 and 965 (as necessary or desired and/or for an RBC storage solution spike assembly 956), inter alia. In keeping with one aspect of the invention, all tubing lines are preconnected before sterilization of the total disposable assembly to assure that maximum sterility of the system is maintained. Note, a highly desirable advantage to preconnection of all of the elements of the tubing circuit including the filter and collection bag sub-assembly 950 involves the complete pre-assembly and then sterilization hereof after assembly such that no sterile docking is later necessary (spike addition of storage solution excepted). Thus, the costs and risks of sterile docking are eliminated. Alternatively, thicker-walled PVC tubing may be employed for approved, sterile docking RBC collector tubing lines 952, 964 and 965, inter alia.

As mentioned, a cassette assembly 110 in the preferred embodiment, may be mounted upon and operatively interface with the pump/valve/sensor assembly 1000 of blood component separation device 6 during use. Further details of an apheresis system set-up including the loading and interaction of a disposable assembly 8/10 with a blood component separation device 6, may be found in the above-listed patents, inter alia, and are not exhaustively repeated here.

Operation of Extracorporeal Tubing Circuit and Blood Component Separation Device Priming and various other operations of the apheresis process are preferably carried out as set forth in the above-listed patents, inter alia. However, certain basic features are also described generally herewith particular reference to the schematic diagram of FIG. 3, as well as with continuing reference to FIGS. 1, 2A and 2B.

Figure 3:
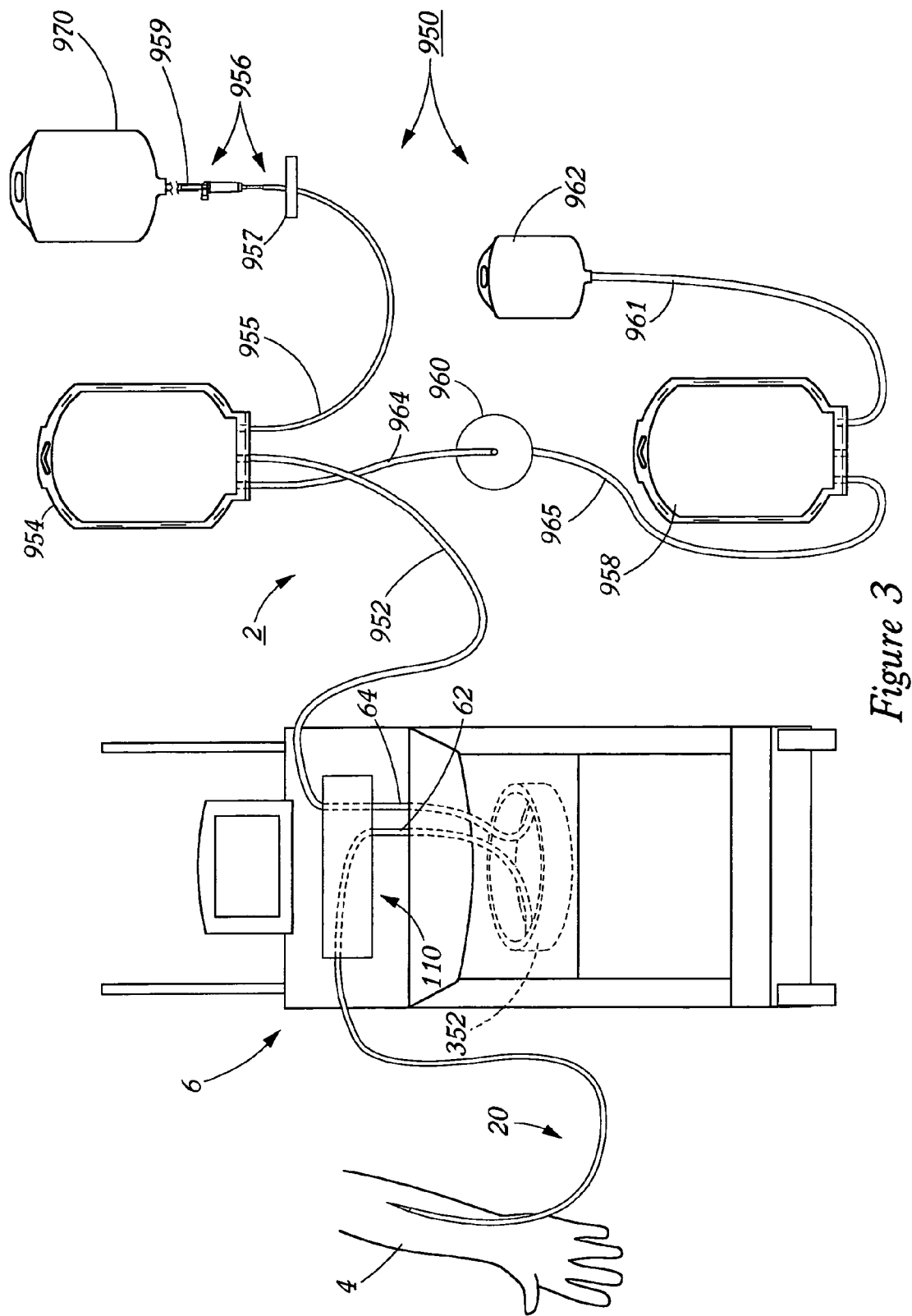
FIG. 3 is another schematic view of an apheresis system together with the filter and collection bag assembly as depicted in FIGS. 2A and 2B as used in the present invention.

For example, during a blood removal submode, whole blood will be passed from a donor 4 into blood removal/return tubing assembly 20 and is then transferred to blood component separation device 6 (see generally FIG. 3). At device 6, the blood is flowed to the processing vessel 352 (schematically shown in dashed lines in FIG. 3) via the cassette assembly 110 and line 62 of the blood inlet/blood component tubing assembly 60 (FIGS. 1 and 2A). Separation processing then occurs preferably on a substantially continuous basis in vessel 352; i.e., blood continuously flows therein, is continuously separated and continuously flows as separated components therefrom. After separation processing in vessel 352 (though separation is continuously occurring), uncollected blood components are transferred from the processing vessel 352 to and through cassette assembly 110, into and may then accumulate in reservoir 150 (FIG. 2A) of cassette 110 up to a predetermined level at which the blood component separation device 6, in a single needle operation, may (though in a continuous system, need not) pause the blood removal submode and initiate a blood return submode wherein these uncollected and/or treated components are returned to the donor 4. As such, these accumulated components may be transferred into the blood return tubing line of blood removal/return tubing assembly 20 and back into the donor 4. During the single needle blood return mode, when the accumulated return blood components in reservoir 150 are removed down to a predetermined level, blood component separation device 6 will then automatically end the blood return submode. This preferably will also automatically serve to reinitiate the blood removal submode. The cycle between blood removal and blood return submodes will then continue until a predetermined amount of RBCs or other collected blood components have been harvested. In an alternative dual needle scheme, as is known in the art, blood may be continually removed from and blood components continually returned to a donor 4. Note, the detailed mechanisms for such operations, including controlling the pumps, for example, are not shown or described in detail herein, particularly not in the schematic view of FIG. 3.

With specific reference to FIG. 2A, in normal operation, whole blood will pass from the donor 4 through the needle and blood removal tubing assembly 20, cassette assembly 110 and blood inlet tubing line 62 to processing vessel 352. The whole blood will then be separated in vessel 352. A platelet stream may be separated herein and be either collected in collector assembly 80 or diverted to reservoir 150. Similarly, separated plasma may also be separated in vessel 352 and either be collected in the container of plasma tubing assembly 90 or diverted to reservoir 150. Further, red blood cells (including potentially some white blood cells) may be separated in and passed from vessel 352 through RBC outlet tubing line 64, through cassette assembly 110 and, in return mode, into reservoir 150. In the preferred alternative, during an RBC collection procedure described hereinbelow, separated RBCs will be delivered to RBC collector tubing assembly 950 through tubing line 952 for collection. The RBC collection protocol may also, and preferably does as described herein, include an RBC filtration process using the preconnected leukoreduction filter 960 and RBC collection bag 958. This procedure will be described further below.

Further details of apheresis processing for the separation of blood into its components may be found in the above-listed patents inter alia and are not substantially repeated here. It may be noted, however, that although alternative separation mechanisms exits, centrifugation is the preferred separation process which is preferably effected by a channel assembly 200 rotated, for example, by a centrifuge rotor assembly 568 in a device 6 (see FIG. 1). Channel assembly 200 would then preferably include a channel housing 204 which would receive the disposable blood processing vessel 352 of tubing circuit 10 (see FIGS. 1 and 2A).

Apheresis Protocol

One preferred protocol, which may be followed for performing an apheresis procedure relative to a donor 4 utilizing the described system 2, will now be summarized. Initially, an operator loads the disposable plastic assembly 8 in and/or onto the blood component separation device 6. According hereto, the operator hangs the various bags (e.g., collection bags 954 and 958, see FIG. 4A, described further below) on the respective hooks (see hook 980 of FIG. 4A, e.g.) of the blood component separation device 6. If one is used, the operator then also loads the cassette assembly 110 on the machine 6 and/or the blood processing vessel 352 within the channel housing 204 as mounted on the centrifuge rotor assembly 568.

With the extracorporeal tubing circuit 10 and the blood processing vessel 352 loaded in the described manner, the donor 4 may then be fluidly interconnected with the extracorporeal tubing circuit 10 by inserting an access needle of the needle/tubing assembly 20 into the donor 4 (see, e.g., FIG. 3). In addition, the anticoagulant tubing assembly 50 is primed (not shown), and blood removal/return tubing assembly 20 is primed preferably with blood from the donor 4 as described in the above-listed patents, inter alia. The blood processing vessel 352 is also primed for the apheresis procedure, preferably also according to the processes described in the same patents. In one embodiment, a blood prime may be used in that blood will be the first liquid introduced into the blood processing vessel 352. During the priming procedure, as well as throughout the remainder of the apheresis procedure, blood is continuously flowed into the vessel 352, blood component types are preferably continuously being separated from each other and are also continuously removed from the blood processing vessel 352, on a blood component type basis. Preferably, at all times during the apheresis procedure, from priming onward, a flow of blood is substantially continuously provided to the blood processing vessel 352 and at least one type of separated component is continually removed.

As RBCs are the component of the most interest in the current invention, the separation protocol will continue with a description of the collection and filtration hereof.

The preferred blood apheresis system 2 provides for contemporaneous separation of a plurality of blood components during blood processing, including at least the separation of red blood cells (RBCs) and plasma, but may also provide for the separation and collection of platelets (as shown here), inter alia. In turn, such separated blood components may be selectively collected in corresponding storage reservoirs or immediately or after a minor delay returned to the donor 4 during respective blood return submodes (or constantly in a two-needle setup). In this regard, and in one approach where more than one blood component is to be collected, such as both plasma (and/or platelets) and RBCs, blood apheresis system 2 may be used to collect plasma (and if desired separated platelets), during a time period(s) separate from the collection of red blood cells. These components may also be collected simultaneously.

In any event, the RBC collection procedure is preferably controlled via control signals provided by blood collection device 6. Such an RBC collection procedure may include a setup phase and a collection phase. During such a setup phase, the blood apheresis system 2 may (as in the preferred embodiment) be adjusted automatically to establish a predetermined hematocrit in those portions of the blood processing vessel 352 and extracorporeal tubing circuit 10 through which separated RBCs will pass for collection during the RBC collection phase. A desirable resulting hematocrit for RBC collection may be between 70 and about 90 or even to 95+, and may preferably be established at about 80. Additionally, blood component device 6 may, during the set-up phase, divert the flow of separated RBCs flowing through outlet tubing line 64 through return tubing loop 172 and into blood return reservoir 150 until the desired hematocrit is established. Then, blood component separation device 6 may also selectively control the diversion of the platelets and plasma into reservoir 150 for return to the donor 4.

In order to establish the desired packing factor and/or hematocrit for the separated RBCs, the operating speed of centrifuge rotor assembly 568 may be selectively established via control signals from blood component separation device 6, and the blood inlet flow rate to vessel 352 may be selectively controlled by blood component separation device 6 controlling the speeds of the respective pump assemblies (not shown or described in detail here). More particularly, increasing the rpms of centrifuge rotor assembly 568 and/or decreasing the inlet flow rate will tend to increase the packing factor and/or hematocrit, while decreasing the rpms and/or increasing the flow rate will tend to decrease the packing factor and/or hematocrit. As can be appreciated, the blood inlet flow rate to vessel 352 may effectively be limited by the desired packing factor or hematocrit.

To establish a desired anticoagulant (AC) ratio, blood component separation device 6 provides appropriate control signals to the anticoagulant pump so as to introduce anticoagulant into the blood inlet flow at a predetermined rate. Relatedly, it should be noted that the inlet flow rate of anticoagulated blood to blood processing vessel 352 is limited by a predetermined, maximum acceptable anticoagulant infusion rate (ACIR) to the donor 4. As will be appreciated by those skilled in the art, the predetermined ACIR may be established on a donor-specific basis (e.g. to account for the particular total blood volume of the donor 4). To establish the desired total uncollected plasma flow rate out of blood processing vessel 352, blood collection device 6 provides appropriate control signals to the plasma (and platelet) pump assembly(ies). This may also serve to increase the hematocrit in the separated RBCs.

In one preferred embodiment, the desired high hematocrit for the separated RBCs will be between about 75 and about 85 and will preferably be about 80; although, again higher hematocrits may be available as well. Then, where a preferred centrifuge rotor assembly 568 defines a rotor diameter of about 10 inches, and where a blood processing vessel 352 is utilized, as described hereinabove, it has been determined that in one preferred embodiment channel housing 204 can be typically driven at a rotational velocity of about 3000 rpms to achieve the desired RBC hematocrit during the setup and red blood cell collection phases. Correspondingly, the blood inlet flow rate to vessel 352 may preferably be established at below about 64.7 ml/min. The desired hematocrit can be reliably stabilized by passing about two whole blood volumes of vessel 352 through vessel 352 before the RBC collection phase is initiated.

To initiate the RBC collection phase, blood component separation device 6 provides an appropriate control signal to the RBC divert valve assembly so as to direct the continuous outflow of the separated high hematocrit RBCs removed from blood processing vessel 352 into the intermediate RBC reservoir 954 through tubing line 952.

As may be appreciated, in the preferred embodiment, the separated RBCs are preferably not pumped out of vessel 352 for collection, but instead are flowed out vessel 352 and through extracorporeal tubing circuit 10 by the pressure of the blood inlet flow to vessel 352. Consequently, trauma to the collected RBCs is preferably minimized.

During the RBC collection phase, the inlet flow into vessel 352 is limited by the above-noted maximum acceptable ACIR to the donor 4. The desired inlet flow rate is also limited by that necessary to maintain the desired packing factor and/or hematocrit, as also discussed. In this regard, it will be appreciated that relative to the setup phase, the inlet flow rate may be adjusted slightly upwards during the RBC collection phase since not all anticoagulant is being returned to the donor 4. That is, a small portion of the AC may remain with the small amount of plasma that is collected with the high hematocrit RBCs in RBC reservoir 954.

According to the present invention, the high hematocrit (high-crit) RBCs are preferably to be filtered as soon as the RBCs are separated or very soon after having been separated within vessel 352. In the substantially continuous centrifugal separation process as described here, a freshly separated stream of RBCs is substantially continually flowing out of the vessel 352, first through tubing line 64, cassette assembly 110 and then through line 952 to the intermediate bag 954 (see FIG. 3). Preferably, these freshly separated RBCs then continue immediately flowing (with perhaps some limited accumulation in bag 954) from bag 954 down through filter 960 and then into collection bag 958 (or also into bag 958a, see FIG. 2C). Thus, in the preferred embodiment, filtration will have begun and is continued simultaneously with or during the overall continuous separation process. More description of this and batch and/or post collection filtration alternatives will be set forth in more detail below.

Note, the phrase freshly-separated is intended to describe the newly-separated blood components in and as they emerge from the mechanical separation system such as device 6 and processing vessel 352. It also includes the state of these same separated components for a reasonable length of time after removal from the mechanical separation device such as from vessel 352. As a general matter, freshly-separated thus relates to the state of these components particularly as they exist at least during the length of the overall separation procedure, but also preferably extends to reasonable periods there beyond. Thus, for example, a first reasonable period may include the entire apheresis procedure which may last up to (and perhaps exceed) two (2) hours during or after which filtration may be begun. Another example may involve a situation in which a red blood cell collection center may, for certain reasons, determine to intermediately collect red blood cell products (in containers 954, e.g.), and then further process/filter these cumulatively in another location (such as the lab) or at set times, as, for example, once or twice each day (thus filtering up to four (4) or perhaps even eight (8) hours after intermediate collection). If reasonable (though not preferred), this time shift could conceivably stretch to even the next day (24 or 36 hours) before the subsequent processing/filtration of the still substantially freshly-separated red blood cell product. Freshly-separated is not intended to refer to previously stored separated red blood cell components. Two further terms used herein have similar distinctions, namely, "recently removed" and "soon after." Recently removed is referred to herein primarily relative to that blood taken from the donor which may be immediately taken and processed in a mechanical separation system, or which may have been taken and held subject to a reasonable non-storage type of delay prior to separation processing. Similarly, "soon after" is used in like manners relative to both of these circumstances as well, as, for example, when separated blood components may be removed from the separation vessel, e.g. soon after separation (whether in continuous or batch mode).

In any event, from the standpoint of the donor 4 and machine 6, following the separation and intermediate collection (including preferably at least the initiation of the filtration) processes of the desired quantity of red blood cells, blood separation device 6 may then provide a control signal to the RBC divert assembly so as to divert any further RBC flow back to the donor 4. Additionally, if further blood processing, by apheresis centrifugation here, is not desired, rinseback procedures may be completed. Additionally, once the minimum desired RBCs have been diverted into assembly 950 and before, during or preferably after filtration completion, the intermediate red blood cell reservoir 954 (and thus the entire sub-assembly 950) may then be disconnected from the extracorporeal tubing circuit 10. If not already begun or even completed, the filtration process may then begin, as described in more detail below. According to the present invention, a storage solution will, preferably after filtration of the RBCs, then be added to the intermediate red blood cell reservoir or bag 954 through a spike connection to a storage solution bag 970 (see FIG. 3) through spike 959, and if used, the opening of the optional frangible connector 968 (see FIG. 2B). This process will also be described further below. Such storage solution may advantageously facilitate storage of the RBCs for up to about 42 days at a temperature of about 1-6 degrees C. In this regard, acceptable storage solutions include a storage solution generically referred to in the United States as Additive Solution 3 (AS-3), available from Medsep Corp. located in Covina, Calif.; and/or a storage solution generically referred to in Europe as SAG-M, available from MacoPharma located in Tourcoing, France.

The storage solution may be and preferably is contained in a separate storage solution bag 970 that can be selectively later interconnected to the intermediate RBC bag 954, preferably through a spike connection 956. In an alternative embodiment, such selective interconnection may be provided via sterile-docking to tubing line 955 as an example (process not shown) utilizing a sterile connecting device (not shown). By way of example, one such sterile connecting device to interconnect tubing line 955 between the storage solution container 970 and the intermediate bag 954, is that offered under the trade name "TSCD" or "SCD™ 312" by Terumo Medical Corporation located in Somerset, N.J. In the preferred alternative, as introduced above, the selective interconnection may be established utilizing a sterile barrier filter/spike assembly 956. The use of such a sterile barrier filter/spike assembly 956 facilitates the maintenance of a closed system, thereby effectively avoiding bacterial contamination. By way of example, the mechanical, sterile barrier 957 filter in such an assembly 956 may include a porous membrane having 0.2 micron pores. A frangible connector 968 (FIG. 2B) may be provided as a further option for selectively opening tubing line 955 for introduction of the storage solution into the RBC filter system.

In order to ensure the maintenance of RBC quality, the intermediate and collection RBC bags 954, 958 the storage solution and the anticoagulant used during blood processing should be compatible. For example, the intermediate and collection RBC reservoirs 954, 958 may be a standard PVC DEHP reservoir (i.e. polyvinyl chloride-diethylhexylphthallate) such as those offered by the Medsep Corporation. Alternatively, a citrated PVC reservoir may be employed. Such a reservoir may utilize a plasticizer offered under the trade name "CITRIFLEX-B6" by Moreflex located in Commerce, Calif. Further, the anticoagulant utilized in connection with the above-described red blood cell collection procedures may be an acid citrate dextrose-formula A (ACD-A).

Nevertheless, according to the present invention as introduced above, before the storage solution is to be added to the collected red blood cells, selective filtering will preferably be performed to remove white blood cells therefrom. More particularly leukoreduction filtering is desired to establish a white blood cell count of at least $<5 \times 10^6$ white blood cells/unit (e.g. about 250 ml.) to reduce any likelihood of febrile non-hemolytic transfusion reactions. Moreover, such filtering will more desirably achieve a white blood cell count of $<1 \times 10^6$ white blood cells/unit to reduce any risk of HLA (i.e. human leukocyte A) sensitization and/or other serious side reactions. Studies have also shown positive effects for pre-storage leukocyte reduction in improving the functional quality of erythrocytes during storage and in decreasing the occurrence of alloimmunization in patients receiving multiple transfusions, as well as being favorable in metabolism reactions such as intra-erythrocyte ATP and/or extracellular potassium levels declining more slowly in filtered products. Perhaps more important is the reduction of transfusion transmitted disease, especially cytomegalovirus (CMV) and/or HIV, inter alia.

Figure 4A:
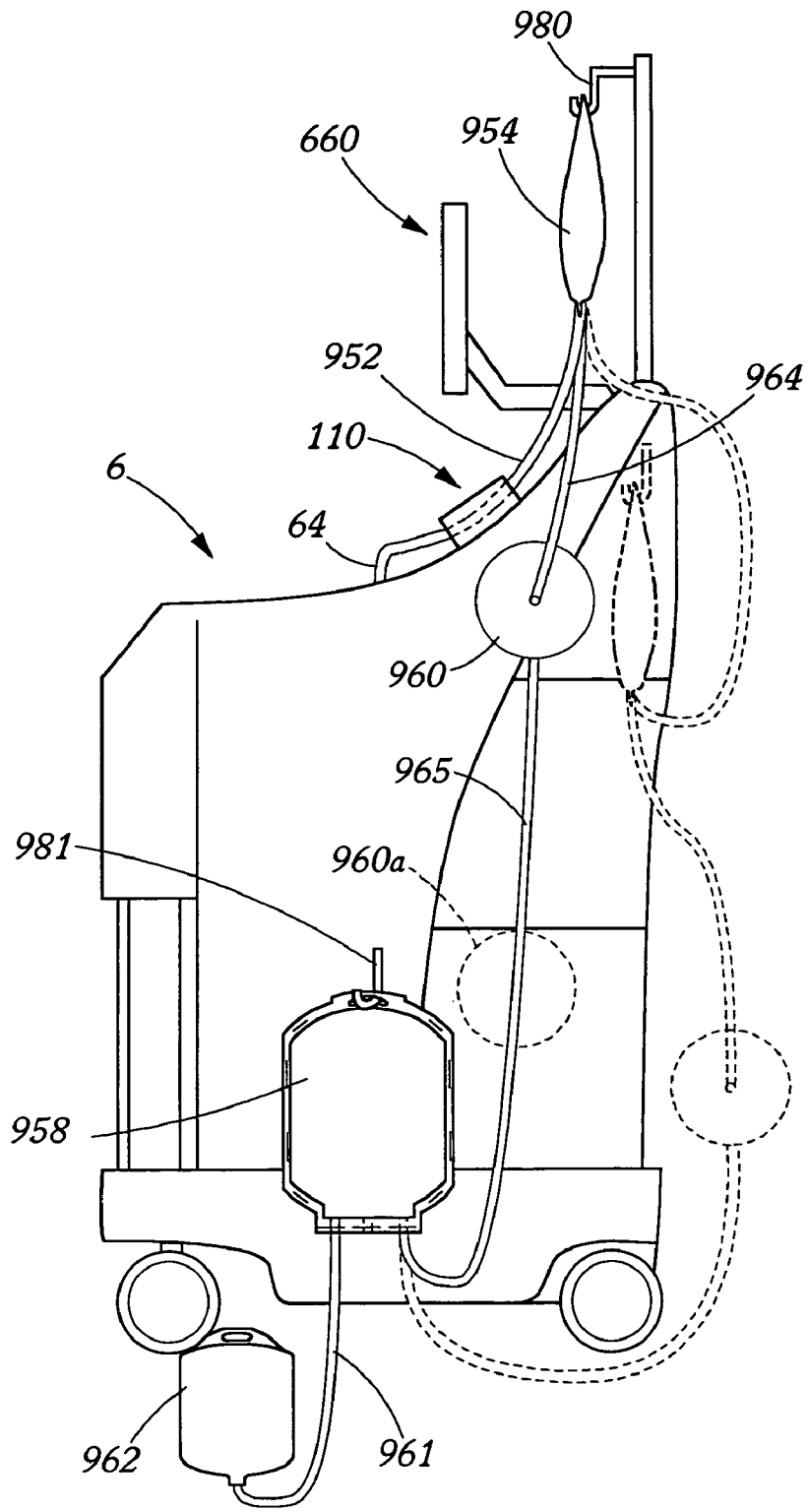
FIG. 4A is a first side elevational view of an apheresis system such as that shown in FIG. 1 used with a filter and collection bag assembly according to the present invention.

Accordingly, the intermediate red blood cell container 954 is, in the preferred embodiment, pre-connected to a red cell filter/collection bag sub-assembly as is shown in FIGS. 1, 2A and 2B (and 2C) so that high hematocrit (preferably Hct approximately equal to or greater than 80), freshly separated red blood cells are preferably gravity transferred from the intermediate bag 954 through filter 960 and into the ultimate RBC collection bag 958. Gravity drainage filtration is shown in FIGS. 3 and 4A, as will be described further below. The red cell filter and collection bag sub-assembly is preferably pre-connected to the intermediate bag 954 as part of the disposable assembly 10 (to avoid the costs and risks of sterile docking) as shown in FIGS. 1, 2A and 2B in accordance with the teachings of this invention, or may be added to the previously existing disposable systems to form a post-manufacturing-connectable disposable assembly using commercially available filter/bag kits such as those available under the trade names "r\LS" manufactured by HemaSure, Inc. located in Marlborough, Mass., or "Sepacell" from Asahi Corp and/or Baxter, Inc. and/or "RC 100", "RC50" and "BPF4" from Pall Corp. located in Glencove, N.Y., inter alia. In either event, the red cell filter/bag sub-assembly is preferably connected (pre- or post-) to the intermediate bag 954 through a tubing line 964 as shown. In one embodiment, this connection contains a frangible connector 967; however, in another and herein preferred embodiment, no such flow stopping connector is disposed between the intermediate bag 954 and filter 960 so that filtration may begin as soon as a flow of freshly separated RBCs reach the intermediate bag 954 as described herein. Note, frangible connector 967 or any other sort of flow stopping mechanism such as a valve or a clamp is an option in lieu of an open line to provide the option of preventing flow directly to the filter 960. This option allows for filtering at some point in time later than simultaneously with or during the intermediate collection in bag 954. Such delayed filtering could be soon after intermediate collection as defined hereinabove.

Nevertheless, referring now primarily to FIGS. 2B, 3 and 4A, the preferred procedure for the filtration of RBCs freshly separated and collected from the apheresis process is as follows. These freshly separated RBCs are still in an undiluted, high-hematocrit state (Hct approximately 80) during the preferred filtration process.

Either simultaneously with the preferred substantially continuous collection process (i.e., as soon as the high hematocrit (high-crit) RBCs reach the intermediate bag 954), or soon after a desired minimum quantity of high-crit RBCs has accumulated in intermediate bag 954, or even totally after collection, but still preferably only soon after the entire collection therein is completed, the RBC collection filtration system 950 is activated to filter the RBCs. If this process is to take place after the collection process is completed, then the RBC sub-assembly 950 can be severed from the extracorporeal tubing circuit 10 at tubing line 952 prior to such filtration (see description below). Otherwise, if, as preferred herein, filtration is to begin during the overall separation process before completion of intermediate collection, then such severing will be performed later in the process.

In either case; simultaneously with the continuous intermediate collection in bag 954 from the separation vessel 352, or soon after completion of the separation and collection process (possibly including such severing), the high-crit RBCs are flowed preferably by gravity drainage through filter 960. As such, intermediate bag 954 is preferably hung at a level above both the collection bag 958 and the filter 960 (see FIGS. 3 and 4A), and frangible connector 967 is then opened (if such a connector or a like optional flow-stopping member is included in sub-assembly 950) so that the collected or continuously collecting high-crit RBCs are allowed to gravity drain downwardly from bag 954 through the filter 960 and into the collection bag 958. A preferred embodiment of this is shown in FIG. 4A, where the intermediate bag 954 is hung from a hook 980 of the machine 6 in known fashion. Tubing line 964 depends downwardly therefrom and is shown as connected to the filter 960, below which depends the next tubing line 965 which is ultimately connected to the collection bag 958 hung from a hook 981 preferably at or near the lowest practical point on the machine 6. Note, bag 954 is shown still connected via tubing line 952 to highlight the preference of continuing to receive freshly-separated RBCs even though filtration has preferably begun.

Any air from bag 958, or air caught between the incoming RBCs and bag 958 is ultimately removed to air removal bag 962 through tubing line connection 961. It is also understood that removal of air may also be achieved by other known (though less desirable here) methods, including, for example, hydrophobic vents and/or by-pass lines. It is desirable to perform the filtering of the RBCs according to the present invention directly on the machine 6 during or very soon after apheresis separation process completion and without pre-cooling or pre-storing the RBCs. In such a case, these procedures are thus performed without the previously conventional steps of cooling and storing overnight at 4 degrees Centigrade.

Figure 4B:
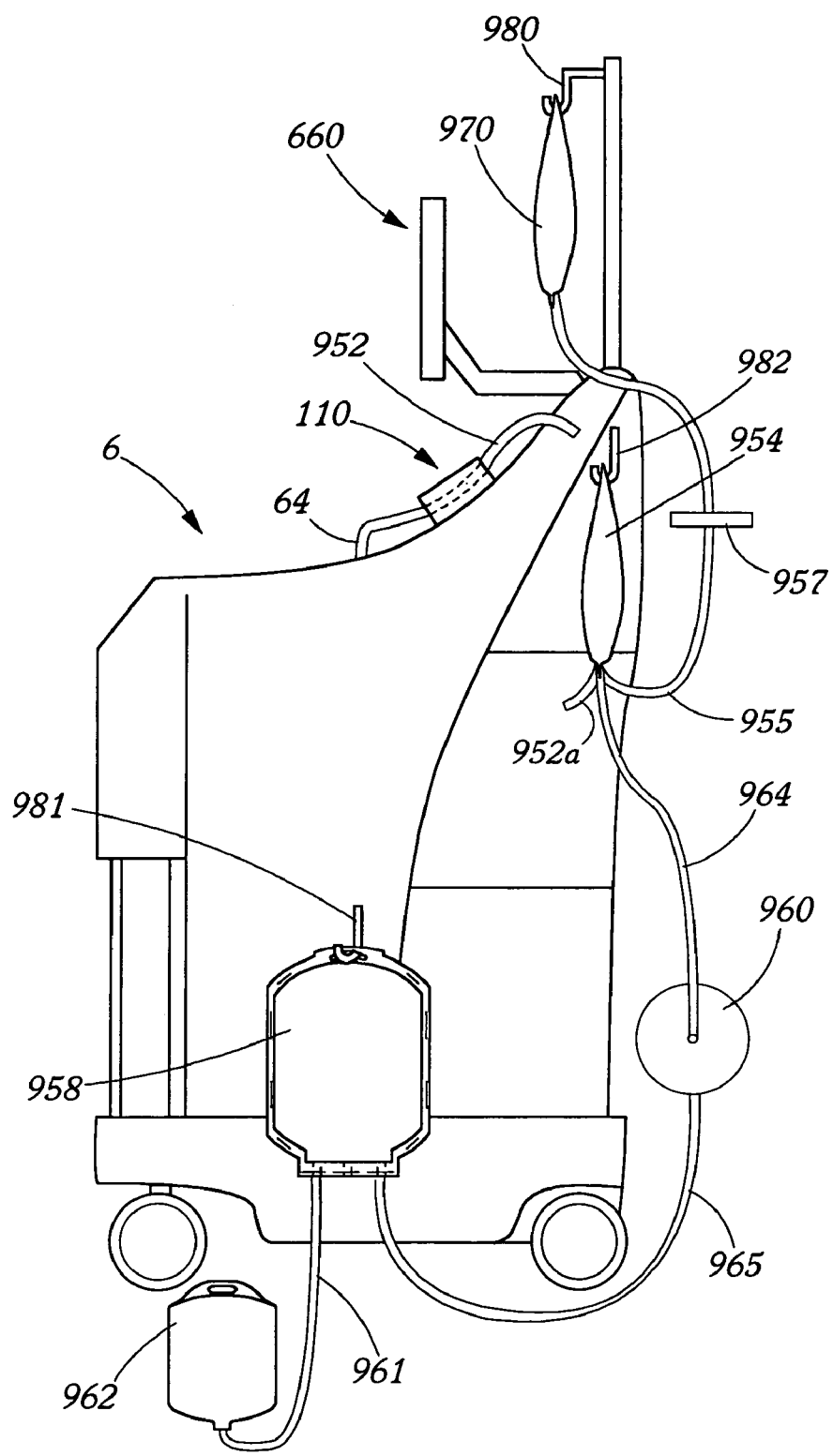
FIG. 4B is a second side elevational view of an apheresis system and a filter and collection bag assembly as in FIG. 4A with an alternative placement of containers and tubing lines.

Then, after completion of the filtration in either of these embodiments, namely, the simultaneous collection and filtering, or in the filtering soon after the intermediate collection completion, storage solution is preferably then added to the intermediate bag 954 through tubing line 955. Again, this is preferably done after completion of the filtration of the high hematocrit, non-diluted RBCs through filter 960. Then, after a storage solution bag 970 has been connected (by spike or sterile welding), as depicted in FIGS. 3 and 4B, the frangible connector 968 is opened (if such an optional flow-stopping member is used; see FIG. 2B) to allow the introduction of the storage solution into the emptied bag 954. The pathway through frangible connector 967 (again, if used) and line 964 remains opened at this point in the procedure and thus the storage solution will flow unabatedly from bag 954 through filter 960 and into the lower collection bag 958 to there mix with and dilute the now filtered high-crit RBCs. Again, all of the steps in operating the RBC filtration system 950 may be performed during or soon after the apheresis component separation procedure and thus need not be subjected to a cooled, time-delayed environment, such as the 4 degrees Centigrade overnight procedures previously thought necessary.

A preferred embodiment of this subsequent storage solution addition step is shown in FIG. 4B, wherein the intermediate bag 954 is shown removed from the upper hook 980 and re-hung on a mid-level hook 982. Then, a storage solution bag 970 can be hung from the upper hook 980 so that when connected and hung as shown in FIG. 4B, storage solution can flow down through tubing line 955 and sterile barrier 957 into intermediate bag 954, from which the storage solution will then flow downwardly from bag 954 through filter 960 and then ultimately into collection bag 958. Note, the embodiment shown in FIG. 4B also includes a depiction of the severed disconnection of intermediate bag 954 from inlet tubing line 952. A stub 952a remains projecting from bag 954. This serves to help depict the herein preferred method of storage solution addition only after at least the procedure for blood separation and intermediate collection of high-crit RBCs from vessel 352 is complete. Preferably, no more separated RBCs are added to the intermediate bag 954 by this point in the procedure; i.e., by the point of adding storage solution. The further preferred steps of having drained all of the RBCs out of bag 954 and having completed filtration thereof through filter 960 prior to the addition of storage solution to bag 954 is not as easily nor separately shown in the Figs. In either event, such a separation may be made by RF sealing the tubing line 952 and then separating in accordance with U.S. Pat. Nos. 5,345,070 and 5,520,218, inter alia, along the RF-sealed portion of tubing line. Other well known methods can also be used to close the tubing line and then also separate the RBC collection system 950 from the remainder of the disposable assembly 10. The RBC collection system 950 which would be remaining after such a severing is shown schematically in FIG. 2B.

The preferred use of the optional two collection bag assembly 950a as shown in FIG. 2C is not much different from the above process. Gravity flow down from intermediate bag 954 through filter 960 to and through each of the branch lines 965, 965a could be used to fill both collection bags 958, 958a simultaneously, or one at a time (wherein a flow stopping member such as a clamp (not shown) could be used to selectively arrest flow into first one then the other of bags 958, 958a until full). Then, however, when a desired double product is filtered and collected accordingly, it may be preferred to provide more control over the storage solution flush and addition process. First, it may be desirable to ensure that the two bags 958, 958a have substantially equal collected volumes, by weight or other means. Excess from one bag may be manipulated into the other bag, by hand compression for example, to flow through the adjoining tubing lines 965, 965a. Then, it may be desired to deliver known amounts of storage solution into the respective bags 958, 958a, via clamping first one tubing line 965, 965a, and then the other during the flush of storage solution through filter 960. Removal of air from the two collection bags into respective air bags 962, 962a would occur as before. Note, the preferred alternative here involves only a single filter 960 for processing the RBCs for both bags 958, 958a. However, a second filter 960a (shown in dashed lines in FIG. 2C) may alternatively be used herewith as well. As shown, intermediately collected RBCs could be made to flow down from intermediate bag 954 through a first filter 960 into a first collection bag 958, until this bag is filled. Then, flow down from bag 954 could be diverted to flow through the alternative second filter 960a to be collected in the second bag 958a. Other alternatives for double RBC product filtration will also be apparent, as for example having separate first and second intermediate bags 954 (not shown), to which separate filters 960, 960a could be attached with their respective collection bags 958, 958a inter alia.

Several advantages can be realized utilizing the preconnected disposable assembly and the above-described procedure for high-crit red blood cell collection and filtration. Such advantages include: consistency in final RBC product volume and hematocrit; reduced exposure of a recipient if multiple units of blood products are collected from a single donor and transfused to a single recipient; reduced time requirements for RBC collection and filtration, including collection of double units of red blood cells if desired, and reduced risks of bacterial and leukocyte contamination. More particularly, several of the reasons why this high-hematocrit (high-Hct or high-crit) with storage solution (e.g., SAG-M) wash approach would not have appeared to work included the expected slow flow of high hematocrit RBCs through the filter 960; the expected risk of blocking the filter 960 with the high-crit RBCs; the previously unknown leukodepletion levels at this high hematocrit; and the apparently likely "wash-out" of WBCs by the storage solution (e.g., SAG-M) through filter 960.

It was conceived and determined to test for possible high-crit filtration success anyway even though the prospect for success appeared unlikely at the outset. The results put serious doubts on the above negative expectations as it was found that: the high-crit RBC units filtered between 10 and 40 minutes, very often between 12 and 18 minutes; leukodepletion before storage solution (SAG-M) wash was good; there was no, or a relatively low, wash-out of WBCs from the filter 960 by the storage solution (SAG-M); and the overall RBC recovery was very high. This last point appears to be a very important advantage; namely, good RBC filtration with very low RBC loss. Another point to be emphasized is the time gained for operators. By performing high-crit filtration immediately during (or even soon after) the overall separation process, the resulting RBC product units are ready to be stored right from the machine without further processing. Operator time is then freed up for performance of other procedures.

While one preferred approach for RBC collection and filtration has been described above, other approaches will be apparent as well. See, for example, FIG. 4A, wherein an alternative placement of the respective filter 960a is shown (in dashed lines) relative to a blood component separation device 6. A further description of this and other alternatives are described below.

Though the following are not in any way intended to limit the present invention, Examples A-E are provided to highlight the efficacy hereof.

EXAMPLE A

Figure 5A:
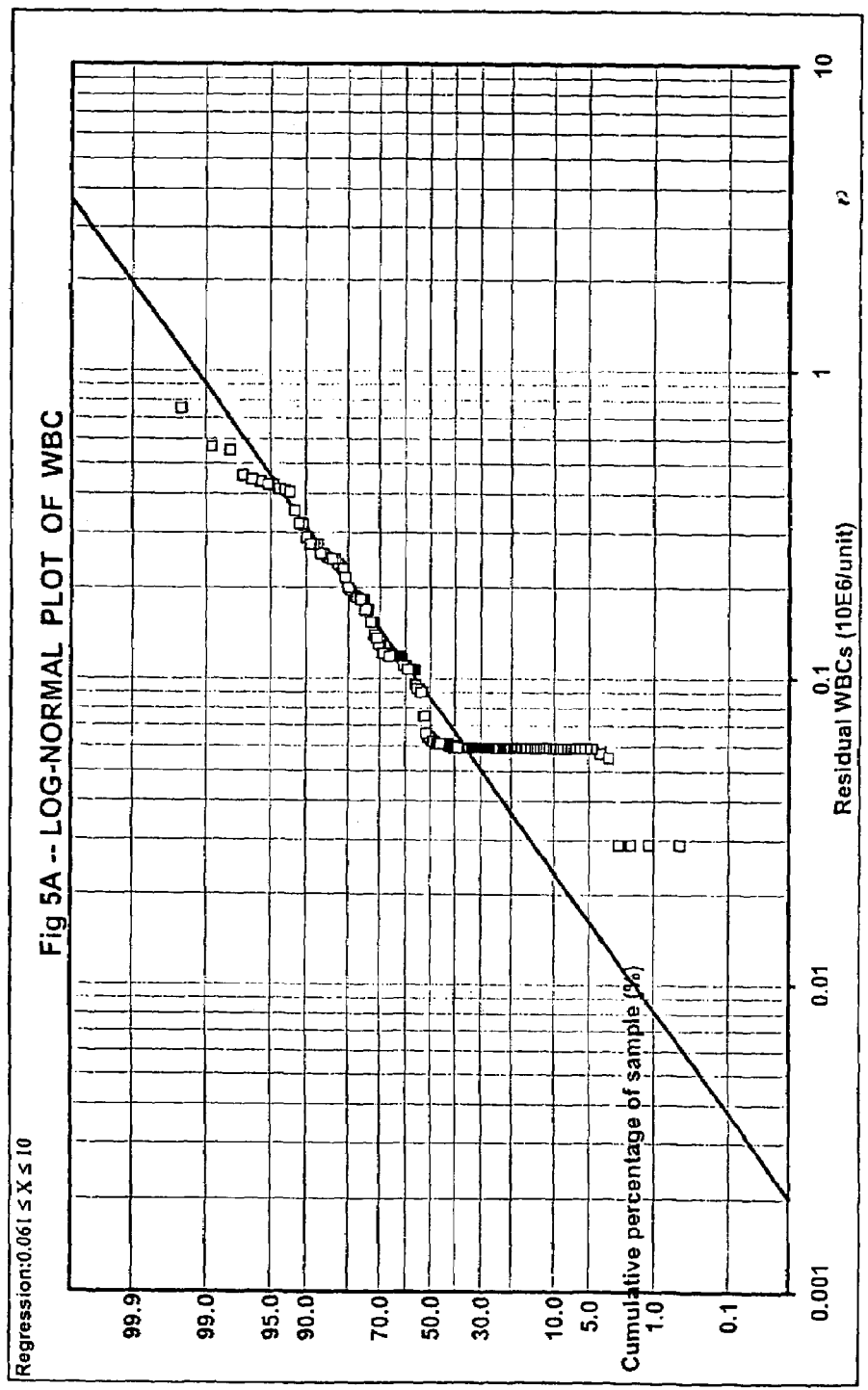
FIGS. 5A-5G are representations of data gathered as described relative to Examples A to E.

Tables 1-3 and FIG. 5A

A multi-center trial was set up to evaluate the performance of the herein described leukodepletion protocol. The methods generally involved filtration at a high hematocrit started during a continuous apheresis separation and collection process. SAG-M storage solution was added after filtration through the RBC filter. Hematocrits and hemoglobin of the filtered RBCs were measured. Deleukocytation (also known as leukodepletion or leukoreduction) was determined by Nageotte. The results of 147 procedures showed that hematocrit and hemoglobin content were normal (57.3±3.0%; 55.1±4.3 g/unit). All products showed excellent leukodepletion ($\leq 0.75 \times 10^6$/unit; 99.31%<$1 \times 10^6$). The conclusion is that immediate, on-line, high hematocrit filtration of red cells collected on a Trima® apheresis system (or the like) results in leukoreduced RBCs which meet the American Association of Blood Banks (AABB) and Council of Europe criteria.

Pre-storage leukoreduction is being used more and more in transfusion medicine. Advantages are well-known and plentiful. It has been established that leukoreduction can reduce the number of non hemolytic febrile transfusion reactions whilst other studies have demonstrated its positive aspects in improving the functional quality of erythrocytes during storage and in decreasing the occurrence of alloimmunization in patients receiving multiple transfusions. Storage studies have further shown that important parameters of metabolism such as intra-erythrocyte ATP and extracellular potassium levels tend to decline more slowly in filtered erythrocyte products which is thought to be linked to the lower levels of contaminating enzymes stemming from lysed leukocytes or platelets in the filtered product. Another important factor in favor of leukodepletion is its reduction of transfusion transmitted disease with especially cytomegalovirus (CMV) being of note.

Currently the level of $<1\times10^6$ WBCs per transfusion is applied as a transfusion standard in many countries. In some countries components with less than $5\times10^6$ WBCs per component are officially considered sufficiently leukodepleted. Previously, filtration after storage with a bedside filter tended to be the predominant method but filtration efficacy turned out to be highly variable even after only brief storage periods at 4° C. Pre-storage leukoreduction is getting to be more and more widely used. Most of these pre-storage filtrations however still take place after a certain hold-period (for instance overnight) and it was observed that better deleukocytation results had been obtained when RBCs were filtered at lower temperatures. These limitations can make pre-storage filtration still relatively time consuming and labor intensive. The aim of this study was to evaluate a new filtration approach in which red blood cells from automated blood collection were filtered directly during on-going continuous separation and collection, particularly also at high collection hematocrit. Determination of the residual WBC levels after filtration was the main objective.

Materials and Methods

Description of the Disposable Assembly and the Collection Procedure:

A Trima® disposable assembly such as assembly 10 (FIGS. 1 and 2A) which is particularly useful with a Trima® apheresis system such as system 2 (FIGS. 1 and 3) for automated collection of platelets/plasma/red cells with a pre-attached leukoreduction filter 960 and filtration sub-assembly 950 was used (FIGS. 2A and 2B). RBCs were collected on the Trima® apheresis system at an 80% target hematocrit. Prior to the collection of the RBCs, the fluid pathway to the filter 960 was opened, allowing immediate filtration from the first milliliter collected in bag 954 onwards. At the end of the filtration 100 ml SAG-M storage solution was added to the RBCs through the filter 960 thus washing out most of the RBCs retained in the filter 960. During the filtration process air was allowed to enter the filter 960. This was to occur during each procedure at the end of filtration before addition of the SAG-M storage solution but also frequently (at least 76% of the runs in this example) at the beginning of RBC collection when the accumulated RBC volume in the intermediate bag 954 (FIG. 2B) is filtered before the apheresis system 2 returned to the collection submode.

During the study care was taken to keep data gathering and analysis well controlled. However, all throughout the study period every participating center retained full freedom in use of its apheresis equipment. This was done intentionally so that the study conditions would be as close as possible to actual routine automated blood collection conditions. The reported data therefore give a good view on how the new high hematocrit filtration protocol performs in a routine setting.

Study Design:

A multi-center trial was set up with 3 blood centers. Per center a total of between 35 and 70 procedures was targeted. In Centers coded A and C, all procedures were routine automated platelet and red blood cell collections, whilst in Center B plasma was collected as well. All centers used the same disposable assemblies 10 with an integrated filter 960 and all apheresis procedures were performed according to local and European regulations. With regard to product yield, Centers A and B targeted collection of 180 ml of RBC in 225 ml collect volume and Center C targeted 200 ml RBC in 250 ml. A summary and overview of the study characteristics are given in Table 1, below.

TABLE 1

PARTICIPATING CENTERS AND TYPES OF PROCEDURE

| CENTER | CODE | NUMBER OF PROCEDURES | PROCEDURE TYPE |
|---|---|---|---|
| Ospedale San Bortolo, Vicenza | A | 58 | Platelet-RBC |
| Centro de Transfusion, Madrid | B | 54 | Platelet-RBC-Plasma |
| Universitätsklinikum, Göttingen | C | 35 | Platelet-RBC |

Laboratory Analysis

All filtered products were weighed individually. The hematocrit of each filtered product after addition of SAG-M was determined using one of three automated cell counters (Coulter EPICS-XL MCL, Sysmex SE900, Sysmex CS). Residual WBC levels were measured using Nageotte counting in 2 centers. Samples were diluted 1 to 10 in Leucoplate (Plaxan) and one grid (40 lanes, 50 µl diluted sample) was counted. One cell observed in one grid of the Nageotte chamber corresponds to 0.2 WBCs per µl. When no WBCs were found, calculations were performed as if 1 WBC was seen. This prevents the final results from being biased toward lower than real contamination and allows logarithmic analysis. Center B used flowcytometry instead, whereby results exceeding 1 cell/µl were double-checked by means of Nageotte. In Center A in addition to the Nageotte counting described above, residual WBCs were also counted using the Terasaki method for the purpose of comparison. Only the data from Nageotte counting were used in the calculations.

Statistical Analysis

The results of the residual WBC counting were analyzed after $\log_{10}$ transformation. As can be seen in the lognormal probability distribution plot (FIG. 5A), many of the observations at or below the minimum detectable level (±60 000 WBCs) corresponding to a concentration of 0.2 WBCs per µl result in a deviation from the straight line. These results were included in the plot but were excluded from the least-squares fit of the regression line in order not to bias the prediction.

Results

General

A total of 147 procedures had been performed in the 3 participating centers (58, 54 and 35 procedures in Centers A, B and C respectively). All filtrations completed without any specific side events noted.

Blood Cell Count

Hematocrit (Hct) and hemoglobin (Hgb) content of the filtered products after SAG-M addition were found to comply with the Council of Europe guidelines: 57.3±3.0% and 55.1±4.3 g/unit respectively. These data are represented in Table 2, below.

Yield

Yield was calculated on the basis of the above hematocrit data and the product volume determined after each filtration. The average efficiency, i.e. the percentage comparing how much actual product was obtained relative to the amount targeted by the machine, was 91.6±4.3%. Breakdown of the efficiency per center is listed in Table 2, below.

TABLE 2

PRODUCT CHARACTERISTICS

| CENTER | Hct (%) | Hgb (G/UNIT) | EFFICIENCY (%) |
|---|---|---|---|
| A | 55.5 ± 2.6 | 54.2 ± 2.8 | 90.7 ± 4.3 |
| B | 58.0 ± 2.8 | 52.8 ± 3.5 | 93.0 ± 4.6 |
| C | 59.1 ± 1.9 | 60.5 ± 3.2 | 90.9 ± 3.3 |

White Cells

FIG. 5A shows the log normal probability plot of the total residual white cell contamination of all procedures. The extrapolated straight line has been obtained by performing a least-squares fit of all data above the detection limit for counting 40 lanes (1 grid) of the Nageotte chamber ($0.06 \times 10^6$). The population is clearly lognormally distributed with a mean of $0.078 \times 10^6$ WBCs per filtered unit (mean±SD, 4.89±0.45). All products showed good leukodepletion: none of the products contained more than $1 \times 10^6$ WBCs. In 76 out of 105 performed Nageotte counts (72%) either one or no WBCs at all were seen in the 40 lanes of the Nageotte chamber which explains the deviation from a straight line below this detection limit. Regression analysis of the linear part of the lognormal probability plot indicates that 99.3% of the procedures can be expected to contain $<1 \times 10^6$ WBC. The median residual WBC level was $0.06 \times 10^6$ per product with a minimum of $0.03 \times 10^6$ and a maximum of $0.75 \times 10^6$ WBCs. Table 3, below, details the break-down for each individual center.

TABLE 3

RESIDUAL WBCs FOR THE DIFFERENT PARTICIPATING CENTERS

| CENTER | MEDIAN ($\times 10^6$) | MAX ($\times 10^6$) | MIN ($\times 10^6$) | PERCENTAGE WITH $<10^5$ |
|---|---|---|---|---|
| A | 0.06 | 0.12 | 0.03 | 88 |
| B | 0.15 | 0.75 | 0.03 | 26 |
| C | 0.06 | 0.46 | 0.06 | 54 |
| A + B + C | 0.06 | 0.75 | 0.03 | 57 |

Discussion

The quantitative aspects of the RBC components obtained after automated blood collection and filtration at high hematocrit are now described. SAG-M storage solution is only added after filtration is finished and is added via the deleukocytation (also known as leukocyte reduction or leukoreduction) filter thus rinsing out part of the RBCs remaining in the filter, tubing lines or the collection bag. Especially the latter might seem to run somewhat contrary to common recognized principles of filtration given the expected risk of washing out the captured WBCs in this way. The data in this study show however that this is not the case. Starting filtration during the automated blood collection results in a finished deleukocytised RBC product shortly after the apheresis procedure is completed.

The results in this study show very good deleukocytation characteristics and demonstrate that filtration at high hematocrit offers an efficient and reproducible way of leukodepleting RBC products. Residual WBCs in all filtered products remained well below the $1 \times 10^6$ limit per unit and more than half of the products were even found to contain less than $1 \times 10^5$ WBCs per unit. Efficiency, expressed as the percentage of the measured yield over the targeted yield, was very good and resulted in more than 90% recovery of the RBC product. The recovery reported here is most probably underestimated. Since the prefiltration product never actually exists as a whole product (a part is already filtered while the product is still being collected), no accurate prefiltration dose can be established. The dose targeted by the Trima® apheresis system was used in the recovery calculations as prefiltration dose. Earlier observations in Europe have shown that actual collected doses by the Trima® apheresis system tend to be a few percent below targeted dose as expressed in absolute volume of red cells. This might be related to differences between hematocrits obtained through centrifuged methodology versus impedance automatic counters. Furthermore, the hyperosmolality of SAG-M might induce some shrinkage of RBCs. In another study where more careful attempts were used to estimate the pre-filtration dose, recoveries were found to be around 97%. There were no signs of wash out of the trapped leukocytes. Other studies have demonstrated normal storage of RBCs using the same filtration and collection approach.

In conclusion, the evaluated high hematocrit filtration protocol has proven to be a reliable and efficient WBC reduction system allowing centers to leukodeplete RBC products in a systematic and fast manner whilst still retaining high quality results. It complements the versatility of the automated blood collection process in that products at the end of the procedure no longer require further processing.

EXAMPLE B

Instructions for Use

Set forth here are more details concerning the preferred procedures to be used in Example A, above, and Examples C-E, except where otherwise noted. Specific reference to the Trima® Automated Blood Component Collection System Operator's Manual or the herein-above listed patent publications is suggested for further specifics regarding the following procedures: setting up the disposable tubing set, performing the collection procedure and, removing the disposable set.

With specific reference to FIGS. 2B, 3 and 4A-4B, the order of preferred steps is as follows:
 1. Break the frangible connector 967 above the filter 960 (if such an optional frangible connector is included in the assembly 10) prior to the start of the apheresis procedure or, if platelets are also to be collected herein, then during the platelet collection phase prior to the start of the RBC collection phase.
 2. Close the air removal clamp 963 near the RBC collection bag 958.
 3. Ensure that the clamp 966 between the filter 960 and the collection bag 958 is open.
 4. Hang the intermediate bag 954 on the I.V. pole hook 980. Hang the collection bag 958 and additional tubing line on the lower hook 981 located on the side of the apheresis machine 6. Ensure that the RBC flow to the collection bag 958 is not impeded. Smooth out any kinks in the tubing line.
 5. Properly label the collection bag 958.
 6. RBC filtration is preferred to occur at room temperature.

7. Once the RBC collection phase has started and the RBCs have entered the filter 960, it is acceptable for air to enter the enter inlet side of the filter 960. Minimize any external physical forces on the RBC intermediate bag 954 and/or the filter 960 or any sudden flow changes. Do not squeeze the RBC intermediate bag 954 to increase flow rates during this step.
8. Filtration is complete when the inlet side of the filter housing 960 is empty.
9. Remove intermediate bag 954 from the apheresis machine 6 pole hook 980 and hang it on the middle hook 982 located on the side of the apheresis machine 6.
10. Hang the additive solution (AS-3, SAG-M) on the I.V. pole hook 980 and spike connect the additive solution bag 970 to the intermediate bag 954 which contained, but is now preferably devoid of, RBCs.
11. Break the frangible connector 968 between the intermediate bag 954 and the spike 959 and allow the additive solution to transfer through the intermediate bag 954 and the filter 960 into the collection bag 958.
12. Filtration flushing is compete when the inlet side of the filter housing is empty.

20. Discard the air removal bag 962 and the air removal clamp 963.

EXAMPLE C

Figure 5B:
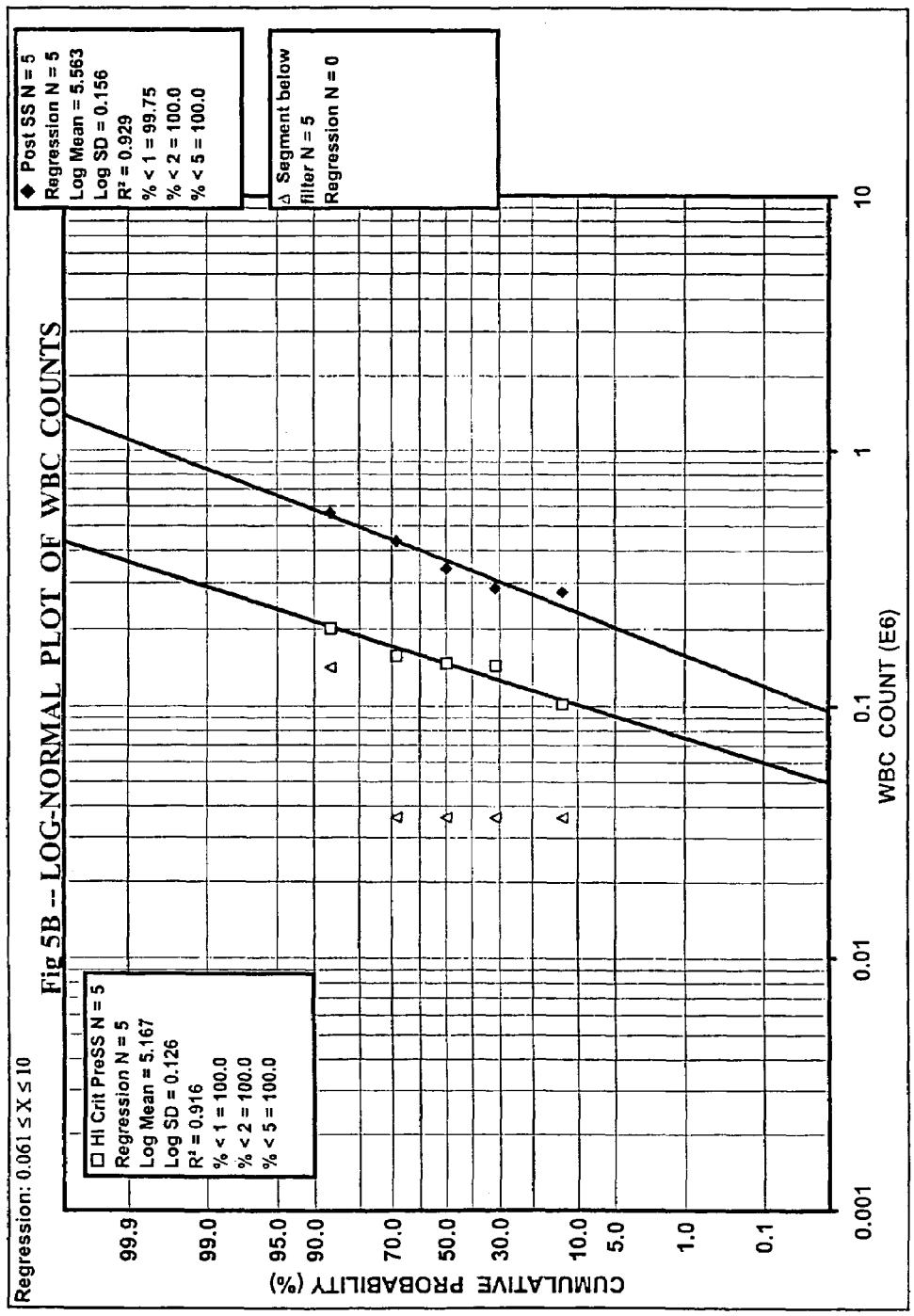

Table 4 and FIG. 5B

The goal in this example was to try filtering simultaneously with the collection of red blood cells. After a small amount of high-crit red cells had been intermediately collected, the frangible connection 967 was broken and the red cells were allowed to flow through the filter 960 into the second bag 958. Then, storage solution was added through the filter 960 according to the above-detailed procedures. Samples for Nageotte counts were taken from the high-crit filtered red cells before storage solution was added and again after the addition of storage solution, and from the segment just below the filter after the storage solution was added. Single and double red blood cell (DRBC) units were collected and used in this example. FIG. 5B is the log-normal plot for these results. The count increases after the storage solution is added through the filter which may imply that the storage solution is washing some cells off the filter.

TABLE 4

| Sample Id | Actual Volume Pre SS | Pre Storage Solution calc'd using 255 Volume | | Pre SS calc'd w/Actual Volumes | Post Storage Solution | | Post SS calc'd w/ Actual Volumes | Segment Post SS | | Donor Pre-Count $\times 10^{\hat{}}3/ul$ |
|---|---|---|---|---|---|---|---|---|---|---|
| | | cells/ul | cells/unit $\times 10^{\hat{}}6$ | cells/unit $\times 10^{\hat{}}6$ | cells/ul | cells/unit $\times 10^{\hat{}}6$ | cells/unit $\times 10^{\hat{}}6$ | cells/ul | cell/unit $\times 10^{\hat{}}6$ | |
| RBCPLTHB1-RBC | 251.0 | 0.8 | 0.20 | 0.20 | 1.6 | 0.57 | 0.56 | 0.4 | 0.14 | 6.00 |
| DRBCHB8-RBCA | 240.0 | 0.6 | 0.15 | 0.14 | 1 | 0.36 | 0.34 | 0.1 | 0.04 | 6.20 |
| DRBCHB8-RBCB | 261.5 | 0.6 | 0.15 | 0.16 | 1.2 | 0.43 | 0.43 | 0.1 | 0.04 | 6.20 |
| DRBCHB9-RBCA | 255.8 | 0.4 | 0.10 | 0.10 | 0.8 | 0.28 | 0.28 | 0.1 | 0.04 | 4.80 |
| DRBCHB9-RBCB | 245.3 | 0.6 | 0.15 | 0.15 | 0.8 | 0.28 | 0.28 | 0.1 | 0.04 | 4.80 |

Example of calculation for RBCPLTHB1-RBC-Hi-crit $$0.8 \frac{\text{Cells}}{\mu l} \times \frac{1 \, \mu l}{10^{-6} \, 1} \times \frac{1 \, l}{1000 \, ml} \times 251 \, ml = 0.2 \, \frac{\text{cells}}{\text{unit}} \times 10^6$$

13. Seal the outlet tubing line 965 next to the outlet port of the filter 960. Discard the intermediate bag 954, the filter 960 and the outlet clamp 966 per standard operating procedures. Weigh the collection bag 958 (include the tubing line 961 and air removal bag 962 that remain connected).
14. Strip the tubing line 965 containing the additive solution into the collection bag 958 preferably three times. If necessary, the emptied line can be sealed off partly when there is no need for all of the available segments.
15. After stripping, do not mix the RBCs as this may cause foam formation and may cause difficulty for later air removal. Mixing should be performed after air removal.
16. For air removal, hold the collection bag 958 vertically with ports up. Open the air removal clamp 963 and squeeze air from the collection bag 958 into the air removal bag 962. Close the air removal clamp 963. Do not express RBCs into the air removal tubing line 961.
17. Mix the RBCs in the collection bag 958 thoroughly.
18. For quality control and/or retention segment sampling, open the air removal clamp 963 and express the RBCs into the air removal tubing line 961. Close the clamp 963.
19. Seal the segmented inlet tubing line 965 of the collection bag 958 and the air removal tubing line 961 per standard operating procedures.

EXAMPLE D

Figure 5C:
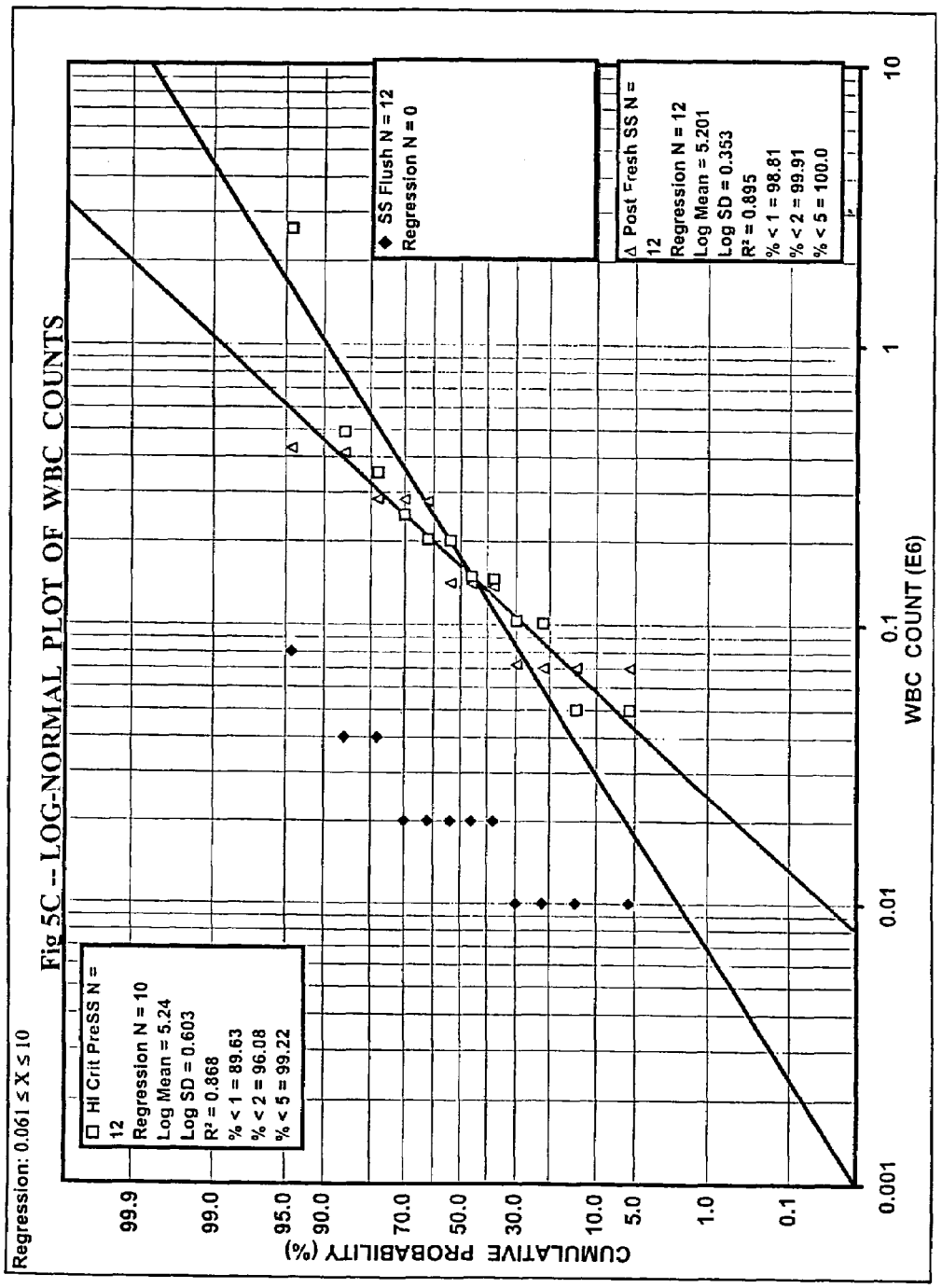
Figure 5D:
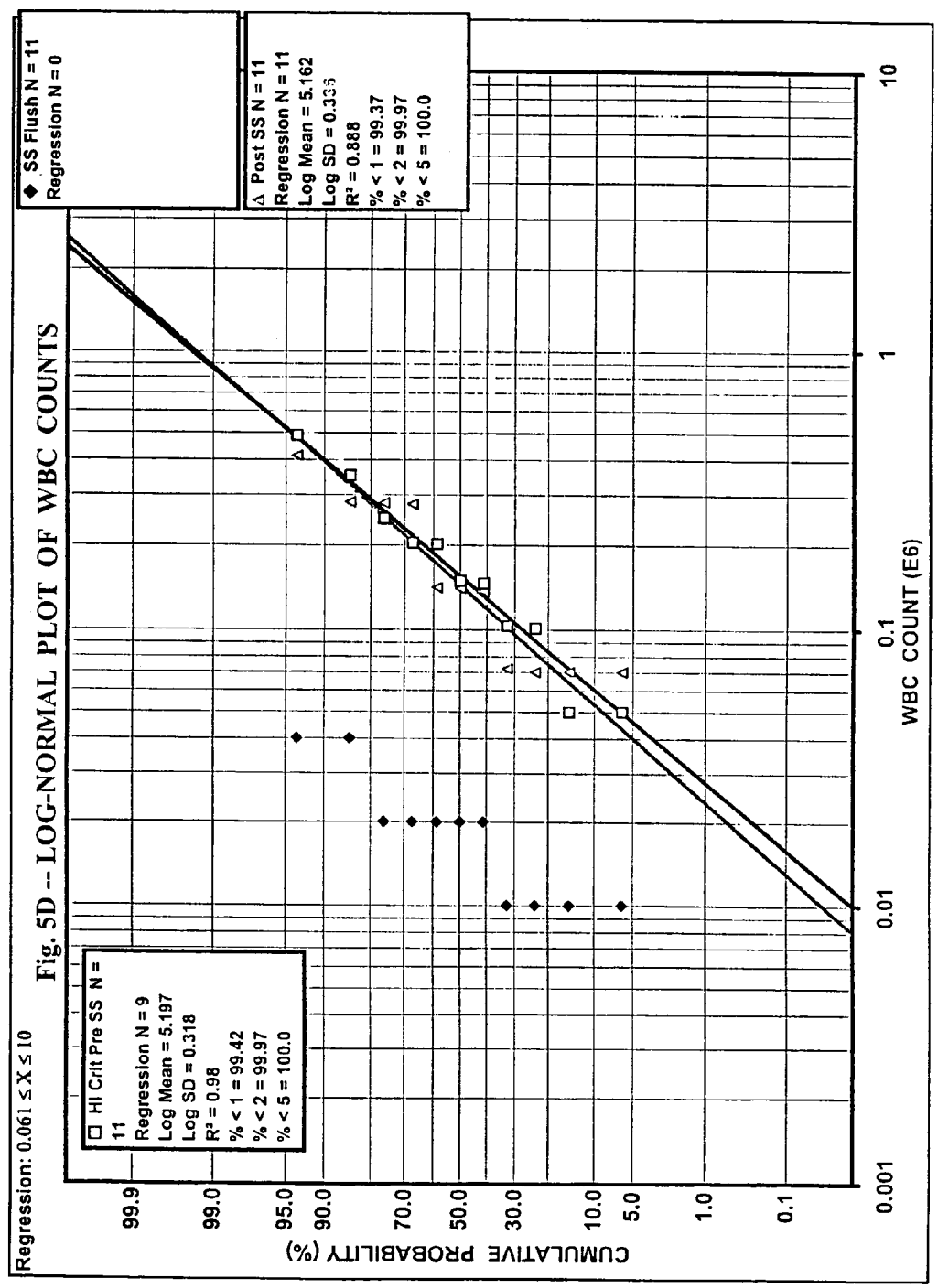

Table 5 and FIGS. 5C and 5D

The data shown in Table 5 were generated by a) sampling the high-crit cells before storage solution was added; b) sampling the storage solution that was flushed through the filter and collected in a separate bag; and c) sampling the high-crit cells after fresh storage solution was added. In these samplings, actual volumes were used to calculate the number of cells per unit.

FIG. 5C graphs the high-crit before and after the addition of storage solution. In this example, the high-crit cell population and the high-crit and storage solution population are more inter-mixed when using actual volumes. There were not enough samples with values above 60,000/unit for the storage solution flush data to appear on the graph, but it appears that the cells have been washed off.

FIG. 5D is a graph of the same data as shown in FIG. 5C removing the high data point in the high-crit population. With the deletion of this data point, the variance in the high-crit count before and after storage solution is added is very small. The pre-storage solution population is the same as the post-storage solution population as they ought to be.

TABLE 5

STORAGE SOLUTION FLUSH THROUGH FILTER INTO SEPARATE BAG
CLEAN STORAGE SOLUTION ADDED TO CELLS

| Sample Id | Actual Volume Pre SS | cells/ ul | Pre Storage Solution calc'd using 255 volume cells/ unit × 10^6 | Pre SS calc'd w/ Actual Volumes cells/ unit × 10^6 | Storage Solution Flush into separate bag cells/ ul | cells/ unit × 10^6 | Post Storage Solution Clean Storage Solution cells/ ul | cells/ unit × 10^6 | Post SS calc'd w/ Actual Volumes cells/ unit × 10^6 | Pre SS + SS Flush cells/ unit × 10^6 | Post SS + SS Flush cells/ unit × 10^6 | Donor Pre-Count ×10^3/ul |
|---|---|---|---|---|---|---|---|---|---|---|---|---|
| DRBCHB10-RBCA | 253.1 | 0.4 | 0.10 | 0.10 | 0.2 | 0.02 | 0.4 | 0.14 | 0.14 | 0.12 | 0.16 | 6.70 |
| DRBCHB10-RBCB | 247.9 | 0.2 | 0.05 | 0.05 | 0.2 | 0.02 | 0.2 | 0.07 | 0.07 | 0.07 | 0.09 | 6.70 |
| DRBCHB13-RBCA | 256.8 | 10.2 | 2.60 | 2.62 | 0.8 | 0.08 | 1.2 | 0.43 | 0.43 | 2.70 | 0.51 | 4.90 |
| DRBCHB13-RBCB | 244.3 | 2 | 0.51 | 0.49 | 0.4 | 0.04 | 1.2 | 0.43 | 0.41 | 0.53 | 0.45 | 4.90 |
| DRBCHB14-RBCA | 250.9 | 1.4 | 0.36 | 0.35 | 0.2 | 0.02 | 0.2 | 0.07 | 0.07 | 0.37 | 0.09 | 5.80 |
| DRBCHB14-RBCB | 249.1 | 0.6 | 0.15 | 0.15 | 0.2 | 0.02 | 0.4 | 0.14 | 0.14 | 0.17 | 0.16 | 5.80 |
| RBCPLAHB2-RBC | 251.0 | 0.8 | 0.20 | 0.20 | 0.1 | 0.01 | 0.8 | 0.28 | 0.28 | 0.21 | 0.29 | 3.60 |
| RBCPLAHB3RBC | 251.0 | 0.2 | 0.05 | 0.05 | 0.1 | 0.01 | 0.2 | 0.07 | 0.07 | 0.06 | 0.08 | 5.50 |
| DRBCHB15-RBCA | 253.3 | 0.8 | 0.20 | 0.20 | 0.2 | 0.02 | 0.8 | 0.28 | 0.28 | 0.22 | 0.30 | 6.50 |
| DRBCHB15-RBCB | 247.8 | 1 | 0.26 | 0.25 | 0.4 | 0.04 | 0.8 | 0.28 | 0.28 | 0.29 | 0.32 | 6.50 |
| DRBCHB16-RBCA | 243.3 | 0.6 | 0.15 | 0.15 | 0.1 | 0.01 | 0.4 | 0.14 | 0.14 | 0.16 | 0.15 | 6.60 |
| DRBCHB16-RBCB | 257.9 | 0.4 | 0.10 | 0.10 | 0.1 | 0.01 | 0.2 | 0.07 | 0.07 | 0.11 | 0.08 | 6.60 |

EXAMPLE E

Figure 5E:
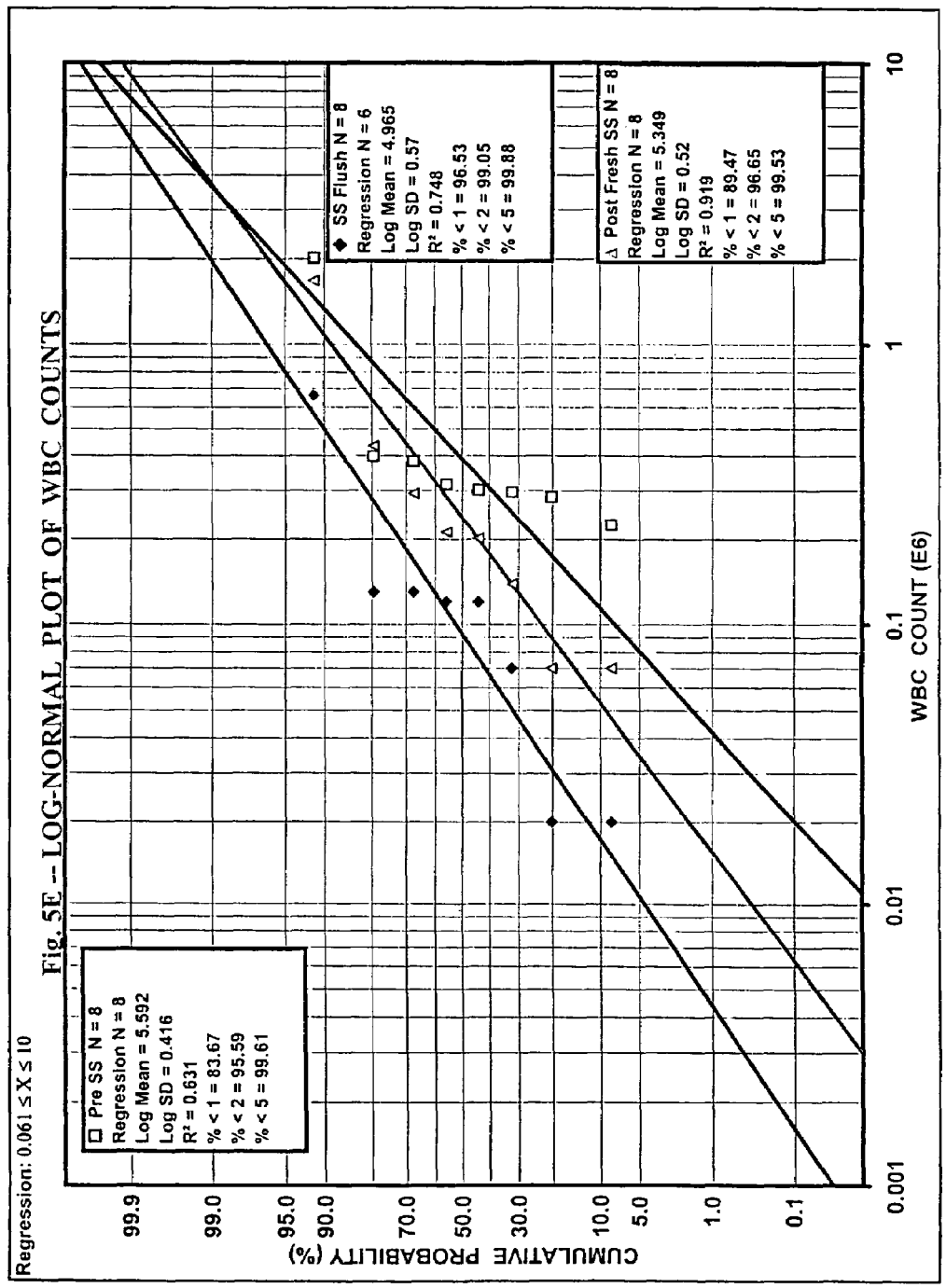
Figure 5F:
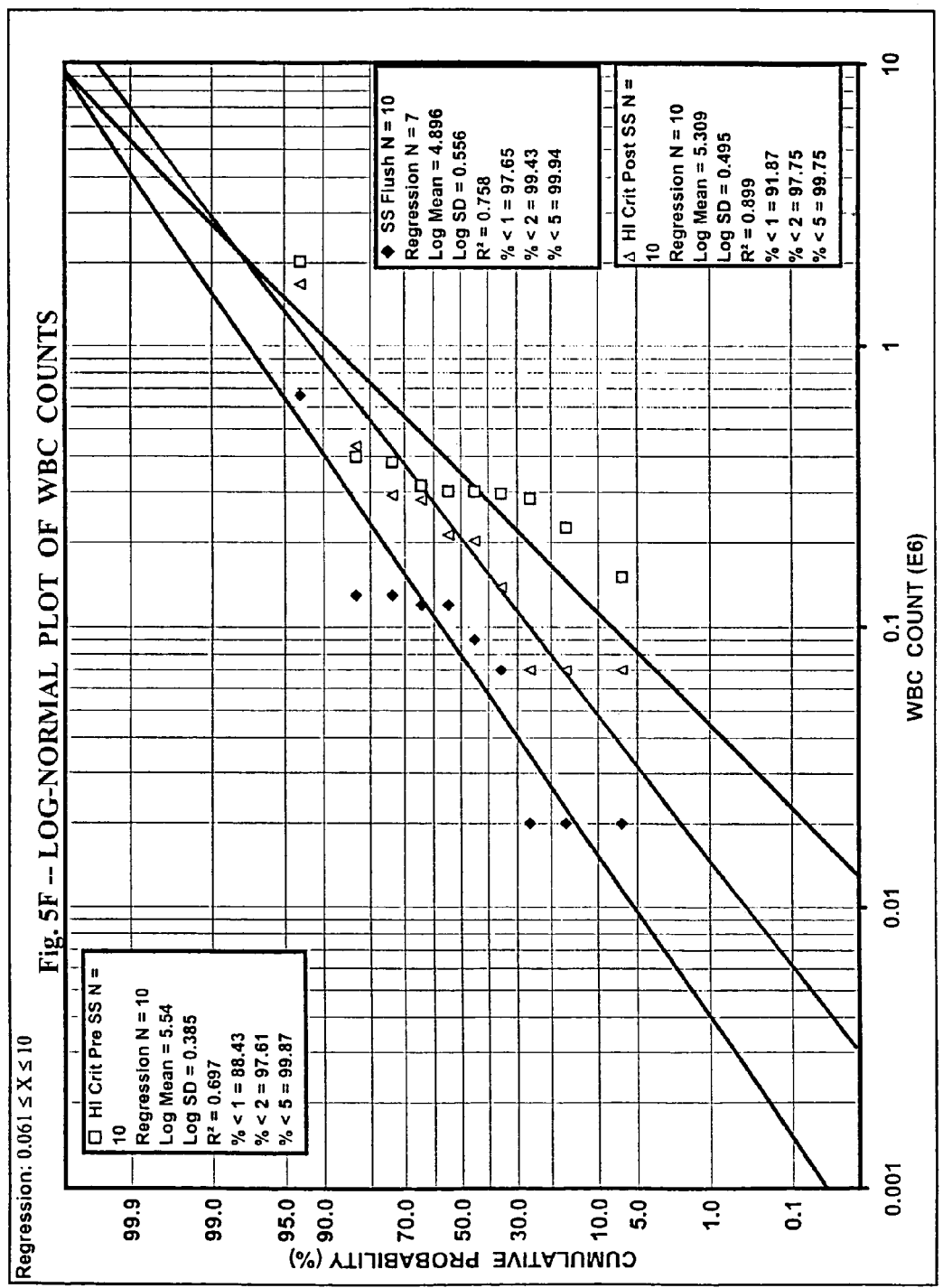
Figure 5G:
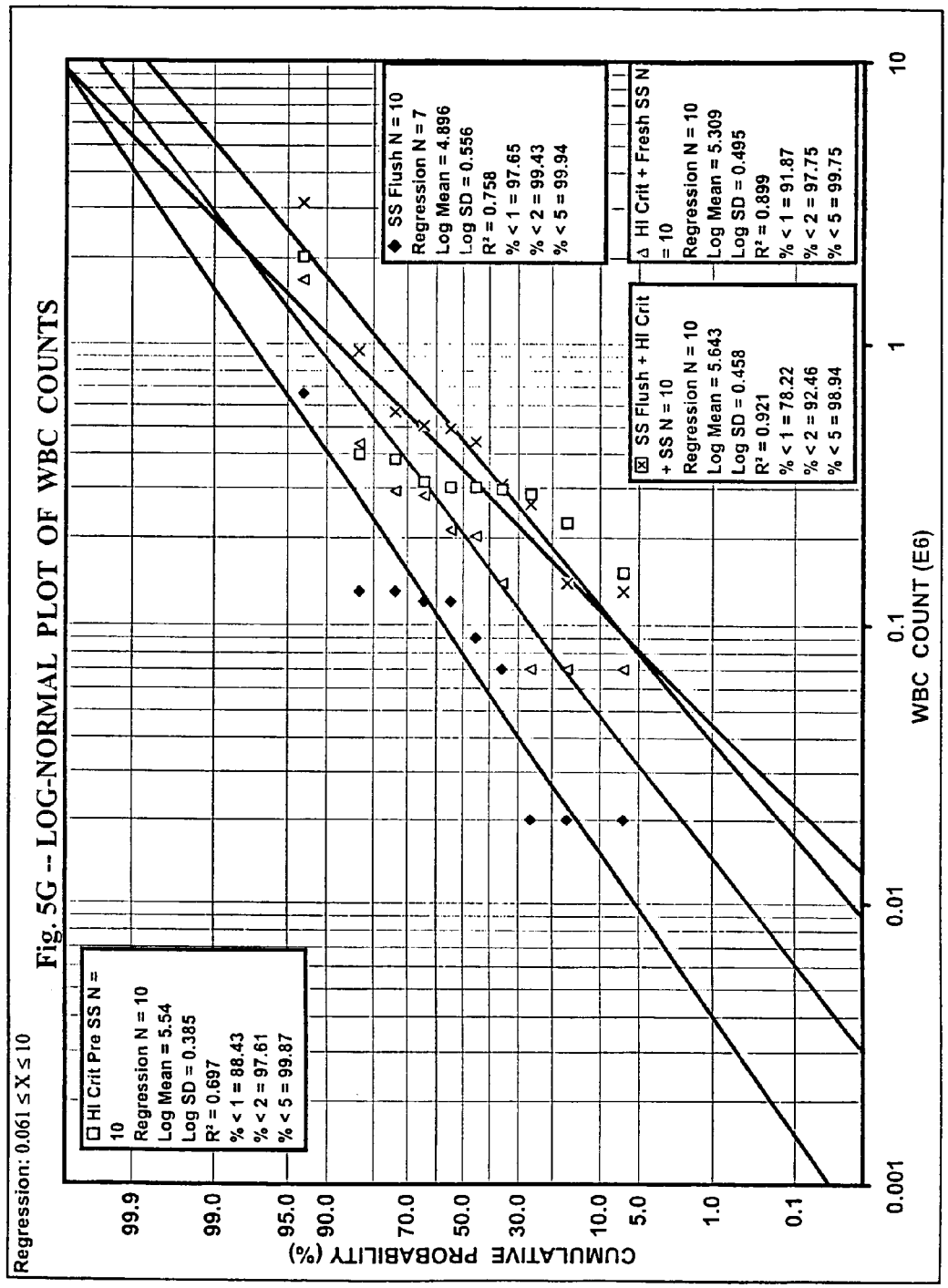

Table 6, FIGS. 5E, 5F and 5G

These data were collected with the same procedure as the preceding examples, but without diluting the high-crit cells with storage solution before counting them. Each plot contains multiple data sets; one with a high-crit before dilution with storage solution, one with the addition of storage solution via a storage solution flush, and one with a further addition of clean storage solution not flushed through the filter. The concentrations calculated with actual volumes were graphed.

FIG. 5E is a regression of storage solution flush data above 61,000. Note that the regression shows a greater difference between the high-crit without storage solution and the high-crit with storage solution than the above counting methods.

FIG. 5F is the same regression of storage solution flush data as shown in FIG. 5E with the addition of two additional filtration samples. The addition of the additional data helps adjust for the skew caused by a single filter failure sample, greatly improving the probabilities.

FIG. 5G includes the same data as FIG. 5F with the addition of data from the white cells from the storage solution flush added to the data for the cells for the high-crit cells and storage solution. The cells/unit ratio was calculated based on the volume of the high-crit storage solution volume. Theoretically, this figure is the number of cells that would have been in the filtered product if the storage solution were flushed through the filter without the filter failure.

TABLE 6

STORAGE SOLUTION FLUSH THROUGH FILTER INTO SEPARATE BAG
CLEAN STORAGE SOLUTION ADDED TO CELLS, BUT STORAGE SOLUTION
ADDED TO HI-CRIT SAMPLES BEFORE COUNTING

| Sample Id | Actual Volume Pre SS | cells/ ul | Pre Storage Solution calc'd using 255 volume cells/ unit × 10^6 | Pre SS calc'd w/ Actual Volumes cells/ unit × 10^6 | Storage Solution Flush into separate bag cells/ ul | cells/ unit × 10^6 | Post Storage Solution Clean Storage Solution cells/ ul | cells/ unit × 10^6 | Post SS calc'd w/ Actual Volumes cells/ unit × 10^6 | Pre SS + SS Flush cells/ unit × 10^6 | Post SS + SS Flush cells/ unit × 10^6 | Donor Pre-Count ×10^3/ul |
|---|---|---|---|---|---|---|---|---|---|---|---|---|
| DRBCHB17-RBCA | 254.02 | 1.5 | 0.38 | 0.38 | 0.7 | 0.07 | 0.6 | 0.21 | 0.21 | 0.45 | 0.28 | 6.9 |
| DRBCHB17-RBCB | 247.03 | 1.2 | 0.31 | 0.30 | 1.2 | 0.12 | 0.4 | 0.14 | 0.14 | 0.42 | 0.26 | 6.9 |
| RBCPLAHB2 | 250.00 | 0.9 | 0.23 | 0.23 | 0.2 | 0.02 | 0.2 | 0.07 | 0.07 | 0.25 | 0.09 | 6.2 |
| DRBCHB18-RBCA | 265.39 | 1.5 | 0.38 | 0.40 | 1.3 | 0.13 | 0.8 | 0.28 | 0.29 | 0.53 | 0.42 | 4.9 |
| DRBCHB18-RBCB | 236.45 | 1.2 | 0.31 | 0.28 | 1.2 | 0.12 | 0.6 | 0.21 | 0.20 | 0.40 | 0.32 | 4.9 |
| DRBCHB19-RBCA | 209.86 | 1.5 | 0.38 | 0.31 | 1.3 | 0.13 | 1.4 | 0.50 | 0.43 | 0.44 | 0.56 | 5.2 |
| DRBCHB19-RBCB | 209.86 | 9.6 | 2.45 | 2.01 | 6.6 | 0.66 | 5.4 | 1.92 | 1.67 | 2.67 | 2.33 | 5.2 |
| RBCPLTHB4 | 251.00 | 1.2 | 0.31 | 0.30 | 0.2 | 0.02 | 0.2 | 0.07 | 0.07 | 0.32 | 0.09 | 5.2 |
| RBCPLTHB5 | 251.00 | 1.2 | 0.31 | 0.30 | 0.9 | 0.09 | 0.2 | 0.07 | 0.07 | 0.39 | 0.16 | 6.5 |
| RBCPLTHB6 | 251.00 | 0.6 | 0.15 | 0.15 | 0.2 | 0.02 | 0.8 | 0.28 | 0.28 | 0.17 | 0.30 | 4.8 |

Numerous further alternative elements and/or embodiments are available. For example, in order to assist an operator in performing the various steps of the protocol being used in an apheresis procedure with the apheresis system 2, the apheresis system 2 preferably includes a computer graphical interface 660 as illustrated generally in FIG. 1. The graphical interface 660 may preferably include a computer display 664 which has "touch screen" capabilities; however, other appropriate input devices (e.g., keyboard) may also be utilized alone or in combination with the touch screen. The graphics interface 660 may provide a number of advantages, but may preferably, at least, assist the operator by providing pictorials of how and/or when the operator may accomplish at least certain steps of the apheresis and/or filtration procedures.

For example, the display screen may sequentially display a number of pictorials to the operator to convey the steps which should be completed to accomplish the filtering procedure described here. More particularly, a pictorial image may be shown on the screen to pictorially convey to the operator when and/or how to hang the respective RBC bags 954 and/or 958 on the machine 6, initially and/or during a subsequent storage solution flush (see FIG. 3, and FIGS. 4A and 4B, for example). One or more pictorials may also be provided to instruct the operator when to break the frangible connector 967 (if included) to begin the filtration process, and/or to visually ensure that the filtration process has appropriately begun simultaneously or during RBC collection. One or more pictorials may also be used to instruct the operator when to connect the spike assembly 956 to a storage solution container 970 and/or when to break the frangible connector 968 (if included) after the RBCs have run through filter 960, to then run the storage solution through the filter 960 and flush any residual RBCs therethrough. One or more pictorials may also be used to instruct the operator when the tube line 952 leading to the intermediate RBC bag 954 should be sealed such that the RBC collect bag 954, and the remaining elements of filter storage assembly 950 may be separated and/or removed from the disposable assembly 10 and/or from the device 6. A similar pictorial can instruct when to seal the tube 965 and/or tube 966 to isolate the RBC collection bag 958 from the rest of the system after the filtration and flushing procedures are completed.

A further advantage of the presently described system includes the manner of handling air. More specifically, the present invention eliminates the prior need for the vents and/or by-pass methods and/or apparatuses of conventional red blood cell filters. Moreover, the present invention is capable of delivering this advantage with no reduction in and/or perhaps an increase in the recovery of RBCs that historically have been trapped inside the filtration device.

A means used by the present invention to deliver this advantage is through the providing of a storage solution flush through the filter after the RBCs have finished filtering therethrough. The storage solution may then be able to wash RBCs caught therein out of the filter and then into the collection bag 958. Prior devices relied upon vents or by-pass-mechanisms to assist in pushing out any RBCs disposed in the filter. Note, though not preferred or needed, vents or by-passes could still be used with the high hematocrit filtration process, and also with and/or in lieu of the storage solution flush after filtration.

In any event, elimination of the need for vents or by-passes also reduces other prior difficulties such as inadvertent allowances of excess air into the system or the requiring of certain predefined lengths of tubing lines on respective sides of the filter. Extra air in the present system will not stop or slow the flow of blood or storage solution through the filter in the present invention. The extra air will either be caught within the intermediate bag 954 or pass through to the collection bag 958 where it can be removed at the end of the overall process to the air bag 962. Then, also, because neither vents nor by-passes are used or needed in the preferred embodiments here, the tubing line lengths important to many prior devices and methods, are not so significant here. Hydrostatic pressures caused by the respective heights of the fluids contained within certain tubing line lengths can counteract the operation of vents; however, this is not problematic here since the preferred subsequent storage solution flush recovers the RBCs from the filter without the previously desired use of a vent or by-pass. Consequently, also, the filter may be disposed at any of a plurality of alternative vertical dispositions between intermediate bag 954 and collection bag 958; see, for example, the dotted line alternative filter marked 960a in FIG. 4A. Operation of the present invention is not hindered by such alternative placements.

The volume of storage solution to be used may, however, be modified depending upon the relative lengths of tubing lines used and/or the air that gets into the system. Thus, if it is known that there is 20-30 ml of dead space in the filter and, say, approximately 20 ml of tubing line between intermediate bag 954 and collection bag 958; and if 100 ml of storage solution is desired to be mixed with the end product RBCs in collection bag 958; then some certain volume more than 100 ml of storage solution would preferably be fed into the system. For example, 140-150 ml would preferably be added; whereby 100 ml of which would go into the collection bag 958 and the remaining 40-50 ml would fill the dead spaces in the tubing line and filter between intermediate bag 954 and collection bag 958.

Note, although a storage solution flush after filtration completion is preferred, alternatives are available here as well. For example, though not preferred, it is possible that storage solution flow into bag 954 may be begun prior to absolute completion of the high-crit RBC filtration. Thus, whatever quantity of RBCs remaining in bag 954 at this point would then be diluted by the storage solution prior to filtration hereof. This is not preferred because it may be that such a diluted end remainder of RBCs might contribute to washing out some WBCs caught in the filter 960.

Other storage solution alternatives include not flushing the storage solution through the filter 960 at all. Such storage solution may be added in other ways; for example by being resident in the ultimate collection bag 958 prior to the inflow of filtered high-crit RBCs thereinto. Or, the storage solution could be flowed past (by-pass) filter 960 directly-into the collection bag 958 during or after the flow of filtered RBCs thereinto.

Note, in the currently described invention, the gravity flow rate out of bag 954 is not very different from the flow rates of RBCs entering intermediate bag 954 from the centrifuge. Thus, a smaller intermediate bag 954 is foreseeably useful herewith as well. By way of example, a intermediate bag 954 could practically be half, or less, than the size of a standard collection bag 958, under present operating conditions.

Another alternative introduced hereinabove involves the use of alternative extracorporeal blood processing systems. Although the preference is for a continuous flow apheresis system, as described here, which includes returning some components back to the donor, batch flow and non-return systems are also useable herewith. For example, a batch mode processor takes in a certain quantity of whole blood, separates the blood into components (in a centrifuge bowl, e.g.) and then passes the separated components to collection containers or back to the donor. The filtration process of the present invention would nevertheless operate in substantially the same manner such that the separated RBCs would nonetheless exist in a substantially high hematocrit state as they are flowed from the separation mechanism, at which point these high-crit separated RBCs could be flowed to an intermediate bag 954 (FIGS. 2B and 3, inter alia), and from there be passed directly or soon thereafter to and through a filter 960 to be collected ultimately in a collection bag 958. Though continuity may be reduced (or substantially removed), the principles of filtration during or soon after the overall separation and collection remain the same. Note, even if flow through the filter 960 stops at any point, or a plurality of points, this is not problematic here where any air entry therein is handled by capture in the air bag 962.

Smaller scale separation and collection devices are also envisioned to be useful herewith. For example, various separation devices (whether centrifugal or membrane or other types) are designed to separate only RBCs and plasma (with the remainder usually remaining in the RBC product), and these can take on smaller scale mechanizations. Nevertheless, the present invention is useful herewith as well in that RBCs separated hereby may also be freshly filtered at high, undiluted hematocrits. The principle of filtering such RBCs during or soon after the overall separation and collection process remains the same here as well. Thus, whether continuous or in batch mode, a flow of high-crit, freshly-separated RBCs can be flowed from the separation device to an intermediate bag 954 and from there immediately or soon after accumulation therein, to and through filter 960 to collection bag 958.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A disposable red blood cell collection assembly for an apheresis system for separating blood into at least one high hematocrit red blood cell component for collection and for the leukoreduction of the high hematocrit red blood cell component;

said disposable assembly comprising:
a blood removal/return assembly for removing blood from and returning any uncollected components to the donor;
a blood processing vessel connected to said blood removal/return assembly, and adaptable to be connected to a separation system for separating blood received from the donor into blood components including the high hematocrit red blood cell component;
an intermediate red blood cell collection bag disparate from yet preconnected via tubing lines to the blood processing vessel;
an openable conduit connected to the intermediate red blood cell collection bag and adapted to be connected to a source of additive solution;
an ultimate red blood cell collection container;
a preconnected leukoreduction filter fluidly disposed between the intermediate red blood cell collection bag and the ultimate red blood cell collection container;
whereby said red blood cell collection assembly is adapted to provide for the passing of undiluted high hematocrit red blood cells from the intermediate red blood cell collection bag through the leukoreduction filter and into the ultimate red blood cell collection container prior to the opening of the openable conduit; and
an air removal bag interconnected to the ultimate red blood cell collection container for receiving air from the ultimate red blood cell collection container; and
wherein the undiluted high hematocrit red blood cells are passed from the intermediate red blood cell collection bag through the leukoreduction filter and into the ultimate red blood cell collection container substantially simultaneously with or during the overall separation process.

* * * * *